(12) United States Patent
Warfield et al.

(10) Patent No.: US 9,492,101 B2
(45) Date of Patent: Nov. 15, 2016

(54) ESTIMATION OF INCOHERENT MOTION PARAMETERS FROM DIFFUSION-WEIGHTED MRI DATA

(71) Applicant: Children's Medical Center Corporation, Boston, MA (US)

(72) Inventors: Simon K. Warfield, Brookline, MA (US); Mordechay Freiman, Boston, MA (US)

(73) Assignee: Children's Medical Center Corporation, Boston, MA (US)

( * ) Notice: Subject to any disclaimer, the term of this patent is extended or adjusted under 35 U.S.C. 154(b) by 0 days.

(21) Appl. No.: 14/431,649

(22) PCT Filed: Sep. 27, 2013

(86) PCT No.: PCT/US2013/062248
§ 371 (c)(1),
(2) Date: Mar. 26, 2015

(87) PCT Pub. No.: WO2014/052793
PCT Pub. Date: Apr. 3, 2014

(65) Prior Publication Data
US 2015/0272467 A1    Oct. 1, 2015

Related U.S. Application Data

(60) Provisional application No. 61/707,762, filed on Sep. 28, 2012.

(51) Int. Cl.
*G06K 9/00* (2006.01)
*A61B 5/055* (2006.01)
(Continued)

(52) U.S. Cl.
CPC ............... *A61B 5/055* (2013.01); *G01R 33/54* (2013.01); *G01R 33/5608* (2013.01); *G01R 33/56341* (2013.01); *A61B 5/4244* (2013.01); *A61B 2576/00* (2013.01)

(58) Field of Classification Search
CPC .................. G06T 7/0012; G06T 2207/30004; G06T 2207/10088; G06T 2207/10092; A61B 5/1128; A61B 2576/00
See application file for complete search history.

(56) References Cited

U.S. PATENT DOCUMENTS 6,219,440 B1 *   4/2001  Schaff ..................... G06F 19/12
                                                    382/128

OTHER PUBLICATIONS

Freiman et al ("Impact of the noise model on intra-voxel incoherent motion (IVIM) parameter estimates in abdominal DW-MRI", 2012).*

(Continued)

*Primary Examiner* — Avinash Yentrapati
(74) *Attorney, Agent, or Firm* — Wolf, Greenfield & Sacks, P.C.

(57) ABSTRACT

Some aspects provide a method of determining a set of parameter estimates for an incoherent motion model from diffusion-weighted magnetic resonance data of a portion of a biological body. The method comprises determining a first set of parameter estimates for a plurality of voxels associated with one or more images based, at least in part, on the diffusion-weighted magnetic resonance data, determining a second set of parameter estimates by stochastically perturbing the first set of parameter estimates, determining a third set of parameter estimates based, at least in part, on the first set of parameter estimates and the second set of parameter estimates, and determining whether at least one criterion associated with the third set of parameter estimates is satisfied.

17 Claims, 13 Drawing Sheets

(51) Int. Cl.
   G01R 33/56   (2006.01)
   G01R 33/563  (2006.01)
   G01R 33/54   (2006.01)
   A61B 5/00    (2006.01)

(56) References Cited

OTHER PUBLICATIONS

Freiman et al., "Impact of the noise model on intra-voxel incoherent motion (IVIM) parameter estimates in abdominal DW-MRI" Proc. Intl. Soc. Mag. Reson. Med. 20 (2012).

Freiman et al., "Characterization of Fast and Slow Diffusion From Diffusion-Weighted MRI and Pediatric Crohn's Disease" Journal of Magnetic Resonance Imaging. 37:156-163 (2013).

Freiman et al., "In vivo assessment of optimal b-value range for perfusion-insensitive apparent diffusion coefficient imaging" Med. Phy. 39(8), Aug. 2012.

Freiman et al., "Quantitative Body DW-MRI Biomarkers Uncertainty Estimation Using Unscented Wild-Bootstrap" Medical Image Computing and Computer-Assisted Intervention. MICCAI 2011, Part II, LNCS 6892, pp. 74-81, 2011.

Lemke et al., "Toward an optimal distribution of b values for intravoxel incoherent motion imaging" Magnetic Resonance Imaging. 29 (2011) 766-776.

Freiman et al., "Reliable Assessment of Perfusivity and Diffusivity from Diffusion Imaging of the Body" Medical Image Computing and Computer-Assisted Intervention. MICCAI 2012, Part I, LNCS 7510, pp. 1-9, 2012.

Freiman et al., "Reliable estimation of incoherent motion parametric maps from diffusion-weighted MRI using fusion bootstrap moves" Medical Image Analysis. 17 (2013) 325-336.

Freiman et al., "Improved Multi B-Value Diffusion-Weighted MRI of the Body by Simultaneous Model Estimation and Image Reconstruction (SMEIR)" Lecture Notes in Computer Science. MICCAI 2013, Part III, LNCS 8151, pp. 1-8, 2013.

Taimouri et al., "Spatially Constrained Incoherent Motion (SCIM) Model Improves Quantitative Diffusion-Weighted MRI Analysis of Crohn's Disease Patients" Abdominal Imaging 2013, LNCS 8198, pp. 11-19, 2013.

Le Bihan et al., "Intravoxel Incoherent Motion Imaging Using Spin Echoes" Magentic Resonance in Medicine. 19, 221-227 (1991).

Koh et al., "Intravoxel Incoherent Motion in Body Diffusion-Weighted MRI: Reality and Challenges" American Journal of Roentgenology. *AJR*2011; 196:1351-1361. (2011).

Powell et al., "The BOBYQA algorithm for bound constrained optimization without derivatives" Technical report NA2009/06, Dep. App. Math. and Th. Physics, Cambridge, England, Aug. 1, 2009 (Aug. 1, 2009), pp. 1-39.

Walker-Samuel et al., "Robust Estimation of the Apparent Diffisuion Coefficient (ADC) in Heterogeneous Solid Tumors" Magnetic Resonance in Medicine. 62:420-429 (2009).

Lempitsky et al., "Fusion Moves for Markov Random Field Optimization" IEEE Transactions on Pattern Analysis and Machine Intelligence. vol. 32, No. 8, Aug. 2010.

International Search Report and Written Opinion for International Patent Application No. PCT/US2013/062248 mailed Mar. 14, 2014.

PCT/US2013/062248, Mar. 14, 2014, International Search Report and Written Opinion.

* cited by examiner f        D*        D b-value = 100 s/mm²        b-value = 200 s/mm²        b-value = 600 s/mm²

ESTIMATION OF INCOHERENT MOTION PARAMETERS FROM DIFFUSION-WEIGHTED MRI DATA

This Application is a national stage application under 35 U.S.C. §371 of PCT International Application No. PCT/US2013/062248, filed Sep. 27, 2013, which claims priority under 35 U.S.C. §119(e) to U.S. Provisional Patent Application Ser. No. 61/707,762 filed Sep. 28, 2012, each of which is herein incorporated by reference in its entirety.

BACKGROUND

Magnetic resonance imaging (MRI) includes techniques for capturing data related to the internal structure of an object of interest, for example, by non-invasively obtaining images of internal structure of the human body. MRI has been widely used as a diagnostic tool in the medical community. MRI exploits the nuclear magnetic resonance (NMR) phenomenon to distinguish different structures, phenomena or characteristics of an object of interest. For example, in biological subjects, MRI may be employed to distinguish between various tissues, organs, anatomical anomalies (e.g., tumors), and/or to image diffusion, blood flow, blood perfusion, etc.

In general, MRI operates by manipulating spin characteristics of subject material. MRI techniques include aligning the spin characteristics of nuclei of the material being imaged using a generally homogeneous magnetic field and perturbing the magnetic field with a sequence of radio frequency (RF) pulses. To invoke the NMR phenomenon, one or more resonant coils may be provided proximate an object positioned within the magnetic field. The RF coils are adapted to generate RF pulses, generally in the form of RF pulse sequences adapted for a particular MRI application, to excite the nuclei and cause the spin to precess about a different axis (e.g., about an axis in the direction of the applied RF pulses). When an RF pulse subsides, spins gradually realign with the magnetic field, releasing energy that can be measured to capture NMR data about the internal structure of the object.

Diffusion-weighted MRI (DW-MRI) is an MR technique sensitive to the incoherent motion of water molecules inside an area of interest. Motion of water molecules is known to be a combination of a slow diffusion component associated with the Brownian motion of water molecules, and a fast diffusion component associated with the bulk motion of intravascular molecules, for example, in the micro-capillaries of tissue vasculature. These phenomena may be characterized via a model referred to herein as the intra-voxel incoherent motion (IVIM) model having a slow diffusion decay parameter (D), a fast diffusion decay parameter (D*), and a fractional contribution (f) of the above two motion components of the DW-MRI signal decay.

IVIM model parameters have shown promise as quantitative imaging biomarkers for various clinical applications in the body including differential analysis of tumors, the assessment of liver cirrhosis, and Crohn's disease. However, conventional implementations of the IVIM model have substantial drawbacks. For example, the IVIM model has conventionally been used to characterize only signal decay related to intra-voxel incoherent motion of water molecules, while both inter-voxel and intra-voxel incoherent motion of water molecules are related to the DW-MRI signal decay.

Moreover, the use of the IVIM model in connection with DW-MRI imaging is conventionally problematic due to the difficulty in determining reliable estimates of the IVIM model parameters (i.e., the fast and slow diffusion decay parameters and the fractional contribution thereof) from the DW-MRI signal/data. In particular, reliable estimates of IVIM model parameters are difficult to obtain for a number of factors including, but not limited to, 1) the non-linearity of the DW-MRI signal decay; 2) the limited number of DW-MRI images as compared to the number of the IVIM model parameters; and 3) the low signal-to-noise ratio (SNR) observed in DW-MRI signals obtained from the body.

Conventional approaches employed to address these difficulties have been generally unsatisfactory such that utilizing the IVIM model has in the past largely been ruled out as a viable solution for clinical settings. FIG. 1A illustrates schematically a conventional approach to determining estimates for the IVIM model parameters. In FIG. 1A (as in the illustrations in FIGS. 1B-1D as well), S represents the signal obtained by performing DW-MRI acquisition and Θ represents IVIM model parameter estimates. The subscripts identify a particular voxel. As such, FIG. 1A shows signal components corresponding to four different voxels being used to independently estimate the IVIM model parameters for the respective voxel. As a result, the approach in FIG. 1A (amongst other problems discussed below) considers only intra-voxel relationships.

Conventionally, a number of approaches have been proposed to address one or more of the above described issues with implementing the IVIM model for DW-MRI data. For example, addressing the non-linearity complication has been attempted by approximating the non-linear DW-MRI signal decay by a log-linear model with the apparent diffusion coefficient (ADC) as the decay rate parameter. However, this simplified model precludes the independent characterization of slow diffusion and fast diffusion components, negatively impacting the ability to characterize and accurately quantify biological phenomena taking place inside the body.

Conventional approaches have attempted to address the relatively low SNR of DW-MRI data in a number of different ways. For example, the SNR may be increased by acquiring multiple DW-MRI images from the patient, averaging the results from the multiple acquisitions and using the averaged DW-MRI signal to estimate IVIM model parameters. FIG. 1B schematically illustrates this approach whereby DW-MRI signals $S_n$ from multiple acquisitions are averaged to estimate the IVIM model parameters Θ for each voxel in the image. However, this requires substantially increased acquisition times, which in clinical settings may be unacceptable from a time and cost perspective. Moreover, such increased acquisition times may be unsuitable for imaging children who generally have difficulty remaining still for long periods of time.

The SNR of DW-MRI may also be increased by averaging the DW-MRI signal over a region of interest (ROI) to generally yield more reliable IVIM parameter estimates. FIG. 1C schematically illustrates this approach whereby DW-MRI signals $S_n$ from a ROI (e.g., a predetermined neighborhood of voxels) are averaged to estimate a single set of IVIM parameter estimates for the ROI. However, the resulting parameter estimates do not adequately reflect heterogeneous environments such as the necrotic and viable parts of tumors, due to averaging the signal over a ROI or neighborhood.

Accordingly, while a number of conventional approaches have been proposed that attempt to address issues with using the IVIM model, such approaches generally remain unsatisfactory in a clinical setting and/or for clinical use, either because the acquisition times are too long, the resulting model parameter estimates are not reliable and/or do not adequately describe or quantify certain tissue structures, characteristics or biological phenomena.

SUMMARY

Some embodiments include a method of determining a set of parameter estimates for an incoherent motion model from diffusion-weighted magnetic resonance data of a portion of a biological body, the method comprising: (A) determining a first set of parameter estimates for a plurality of voxels associated with one or more images based, at least in part, on the diffusion-weighted magnetic resonance data; (B) determining a second set of parameter estimates by stochastically perturbing the first set of parameter estimates; (C) determining a third set of parameter estimates based, at least in part, on the first set of parameter estimates and the second set of parameter estimates; (D) determining whether at least one criterion associated with the third set of parameter estimates is satisfied; (E) performing acts (B)-(C) using the third set of parameter estimates as the first set of parameter estimates if the at least one criterion is not satisfied; and (F) outputting an indication of the third set of parameter estimates if the at least one criterion has been satisfied.

Some embodiments include at least one computer readable storage medium encoded with a plurality of instructions that, when executed by at least one computer processor, perform a method of determining a set of parameter estimates for an incoherent motion model from diffusion-weighted magnetic resonance data of a portion of a biological body, the method comprising: (A) determining a first set of parameter estimates for a plurality of voxels associated with one or more images based, at least in part, on the diffusion-weighted magnetic resonance data; (B) determining a second set of parameter estimates by stochastically perturbing the first set of parameter estimates; (C) determining a third set of parameter estimates based, at least in part, on the first set of parameter estimates and the second set of parameter estimates; (D) determining whether at least one criterion associated with the third set of parameter estimates is satisfied; (E) performing acts (B)-(C) using the third set of parameter estimates as the first set of parameter estimates if the at least one criterion is not satisfied; and (F) outputting an indication of the third set of parameter estimates if the at least one criterion has been satisfied.

Some embodiments include at least one computer, comprising at least one computer processor, and at least one storage device configured to store a plurality of instructions that, when executed by the at least one computer processor, perform a method of determining a set of parameter estimates for an incoherent motion model from diffusion-weighted magnetic resonance data of a portion of a biological body, the method comprising: (A) determining a first set of parameter estimates for a plurality of voxels associated with one or more images based, at least in part, on the diffusion-weighted magnetic resonance data; (B) determining a second set of parameter estimates by stochastically perturbing the first set of parameter estimates; (C) determining a third set of parameter estimates based, at least in part, on the first set of parameter estimates and the second set of parameter estimates; (D) determining whether at least one criterion associated with the third set of parameter estimates is satisfied; (E) performing acts (B)-(C) using the third set of parameter estimates as the first set of parameter estimates if the at least one criterion is not satisfied; and (F) outputting an indication of the third set of parameter estimates if the at least one criterion has been satisfied.

BRIEF DESCRIPTION OF DRAWINGS

Various aspects and embodiments will be described with reference to the following figures. It should be appreciated that the figures are not necessarily drawn to scale.

DETAILED DESCRIPTION

As discussed above, DW-MRI has the potential to provide important new insights into physiological and microstructural properties of the body. The conventional IVIM model relates the observed DW-MRI signal decay as a function of the b-values used to acquire the images to parameters that, for example, reflect blood flow in the capillaries, (D*), the capillaries volume fraction (f), and diffusivity (D). However, the conventional IVIM model techniques commonly use independent voxel-wise fitting of the model parameters to the data and therefore do not account for inter-voxel interactions. Therefore, conventional techniques frequently lead to imprecise parameter estimates, which has hampered the practical usage of DW-MRI.

Figure 1D:
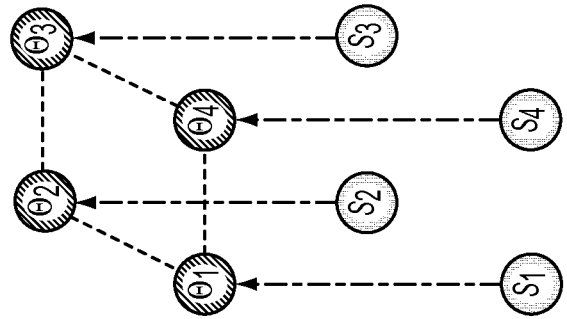
FIG. 1D schematically illustrates an approach that accounts for inter-voxel and intra-voxel interactions by enforcing a measure of spatial homogeneity, in accordance with some embodiments.
Figure 1C:
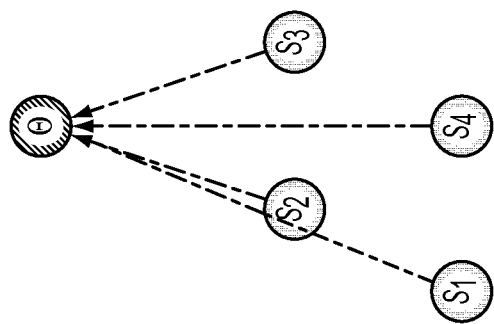
FIGS. 1A-1C schematically illustrate a number of conventional approaches to estimating IVIM model parameters for DW-MRI data.
Figure 1B:
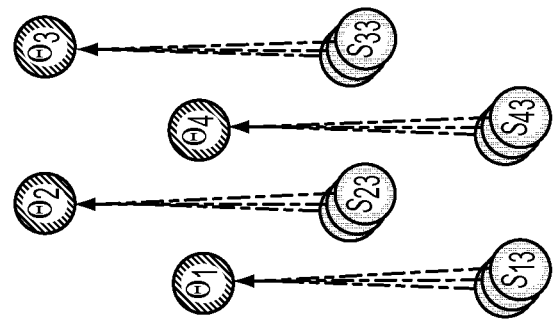
Figure 1A:
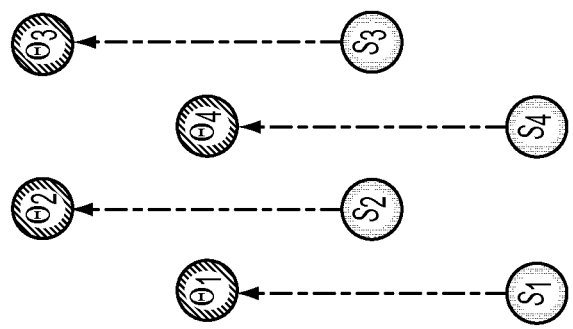

The inventors have developed an incoherent motion (IM) model and techniques for estimating the model parameters that accounts for both intra-voxel and inter-voxel interactions. FIG. 1D illustrates schematically estimating model parameters by considering adjacent voxels, and in particularly, enforcing a measure of spatial homogeneity. Additionally, the inventors have developed techniques that facilitate improving the accuracy and precision of estimating model parameters for the IM model. According to some embodiments, model parameter estimates are iteratively improved by stochastically perturbing a current set of model parameter estimates to obtain a proposal set of model parameter estimates. Stochastic perturbation refers herein to perturbing the values of a set of model parameter estimates such that at least one variable of the perturbation is random. For example, the current set of model parameter estimates may be perturbed so that the direction in which values of the model parameter estimates are perturbed is assigned randomly. Alternatively, or in addition to, the amount by which values of the model parameter estimates are perturbed may also be assigned randomly. Examples of stochastically perturbing model parameter estimates are discussed in further detail below.

According to some embodiments, the current set of model parameter estimates and the proposal set of model parameter estimates (obtained via stochastically perturbing the current set of model parameter estimates) are fused by selecting model parameter estimates from either the current set or the proposal set to form a fused set of model parameter estimates. The fused set of model parameter estimates may be selected based on which model parameter estimates provide a better fit to the observed DW-MRI data. According to some embodiments, the fused set of model parameter estimates are selected based on minimizing an energy function using a graph min-cut algorithm, as discussed in further detail below.

According to some embodiments, to account for inter-voxel interactions a spatial homogeneity constraint may be utilized when estimating model parameters. For example, a spatial homogeneity constraint may be utilized to determine an initial set of model parameter estimates and/or may be utilized when fusing a current set and a proposal set of model parameter estimates. For example, with respect to utilizing a spatial homogeneity constraint when fusing, selecting model parameter estimates from the current set and the proposal set may involve preferentially selecting model parameter estimates that are similar to those in adjacent voxels and/or in a predetermined voxel neighborhood. According to some embodiments, a measure of spatial homogeneity is enforced in a Bayesian framework utilizing a spatial homogeneity prior to account for at least some inter-voxel interactions.

Following below are more detailed descriptions of various concepts related to, and embodiments of, estimating incoherent motion model parameters from DW-MRI data. It should be appreciated that various aspects described herein may be implemented in any of numerous ways. Examples of specific implementations are provided herein for illustrative purposes only. In addition, the various aspects described in the embodiments below may be used alone or in any combination, and are not limited to the combinations explicitly described herein.

Figure 2:
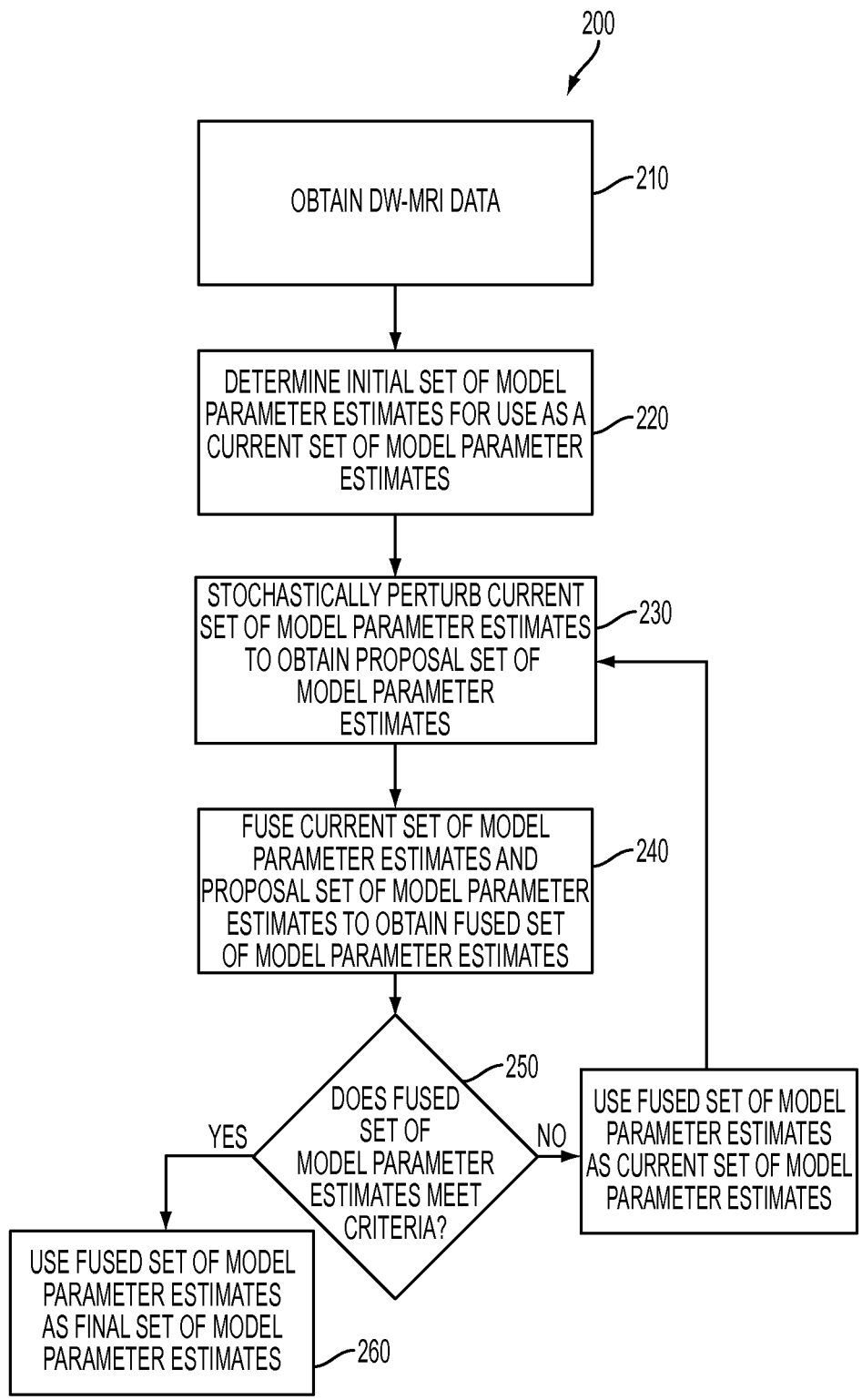
FIG. 2 is a flow chart illustrating a method of estimating incoherent motion model parameters, in accordance with some embodiments.

FIG. 2 illustrates a method of iteratively determining estimates for parameters of an incoherent motion (IM) model, in accordance with some embodiments. In act 210, DW-MRI data is obtained. The DW-MRI data may be obtained by performing one or more DW-MRI acquisition processes on a magnetic resonance (MR) scanning device (e.g., an MR scanning device as described below in connection with FIG. 4), or the DW-MRI data may be obtained from a location where it was stored on electronic media subsequent to, for example, DW-MRI image acquisition previously performed. According to some embodiments, the DW-MRI data includes DW-MRI data acquired at a plurality of non-zero b-values, though in some embodiments, the DW-MRI data may have been acquired at a single non-zero b-value. As such, the DW-MRI data may be obtained from anywhere and in any manner, as obtaining DW-MRI data is not limited to any particular source or any particular manner of acquisition.

In act 220, an initial set of model parameter estimates of a corresponding IM model are determined based on the obtained DW-MRI data. For example, each of the plurality of parameters of the IM model may be estimated for each of a plurality of voxels associated with one or more images to be derived from the DW-MRI data. The initial set of model parameter estimates may be obtained using any suitable algorithm capable of producing estimates for the parameters of the IM model being utilized, some examples of which are discussed in further detail below. According to some embodiments, the IM model includes a slow diffusion parameter, a fast diffusion parameter, and a fractional contribution parameter. However, an IM model may include more, fewer or different model parameters depending on the model being utilized.

According to some embodiments, determining the initial set of model parameter estimates for the IM model includes employing a spatial homogeneity constraint between adjacent and/or neighborhood voxels. By implementing a spatial homogeneity constraint, inter-voxel incoherent motion interactions may be accounted for in the initial set of model parameter estimates. However, employing a spatial homogeneity constraint is not a requirement and some embodiments may estimate model parameters for voxels independently. The initial set of model parameter estimates may be used as the current set of model parameter estimates for a first iteration, as discussed in further detail below.

In act 230, the current set of model parameter estimates are stochastically perturbed to obtain a proposal set of model parameter estimates for the IM model. As discussed above, stochastic perturbation refers to perturbing the values of model parameter estimates wherein at least one variable of the perturbation is random. According to some embodiments, the direction in which each of the model parameter estimates is perturbed is random. In particular, it is randomly determined for each model parameter for each voxel whether to add to or subtract from the current model parameter estimate. According to some embodiments, the amount that is added to or subtracted from each respective model parameter estimate for each voxel is also random.

According to other embodiments, the amount that is added to or subtracted from each respective model parameter is computed deterministically, for example, based on the DW-MRI data, based on the type of the parameter, based on the voxel or neighboring voxels and/or based on some other criteria, some examples of which are described in further detail below. In this manner, new proposals for the model parameter estimates are obtained via stochastic perturbation of the current set of model parameter estimates. It should be appreciated that the model parameters may be perturbed in other ways to affect a random perturbation of a set of parameter estimates.

In act 240, the current set of model parameter estimates and the proposal set of model parameter estimates are fused. According to some embodiments, fusing involves selecting at least some model parameter estimates from either the current set or the proposal set of model parameter estimates. According to some embodiments, fusing involves determining an estimate for at least some model parameters based on the respective estimates from the current set and the proposal set (e.g., by averaging, weighted averaging, scaling, etc.). In general, fusing involves selecting a fused set of model parameter estimates that better fits the observed DW-MRI data, as discussed in further detail below.

According to some embodiments, fusing is performed by selecting the model parameter estimate either from the current set or the proposal set for each model parameter for each voxel to obtain a fused set of model parameter estimates that better fits the acquired DW-MRI signals/data. Selecting such a fused set of model parameter estimates may be performed, for example, by minimizing an energy function (e.g., an energy function that evaluates the likelihood of a given estimate based on the observed DW-MRI data). As such, a generally optimal set of model parameters may be selected from the current and proposal sets of model parameter estimates. The resulting fused set of model parameter estimates may be used as a new current set of model parameter estimates or as the final set of model parameter estimates based on evaluating the fused set against a given criteria, as discussed below in act 250.

According to some embodiments, a fused set of model parameter estimates may be determined using a binary graph-cut technique wherein the current set and proposal set of model parameter estimates are represented as nodes and the likelihood of a respective model parameter estimate given the observed DW-MRI data is represented by the corresponding edge weight. The optimal fusion between the current set and the proposal set of model parameter estimates may then be found by solving the corresponding graph min-cut problem, as discussed in further detail below. However, a generally optimal fused set of model parameter estimates may be determined in any suitable manner, as doing so is not limited to any particular algorithm or optimization technique.

According to some embodiments, fusing the current set and the proposed set of model parameter estimates is performed using a spatial homogeneity constraint to enforce a measure of similarity between model parameter estimates for adjacent voxels and/or voxels in a predetermined neighborhood. The spatial homogeneity constraint may be enforced using a spatial homogeneity prior in a Bayesian framework, as discussed in further detail below. For example, in the graph min-cut optimization described above, edge weights may be formulated to penalize differences between model parameter estimates in adjacent voxels. However, a spatial homogeneity constraint may be enforced in other ways depending on the optimization technique utilized to determine the fused set of model parameter estimates, and employing a spatial homogeneity constraint is not limited for use with any particular implementation. A spatial homogeneity constraint, however employed, may facilitate modeling inter-voxel relationships and, in particular, inter-voxel incoherent motion interactions.

As a result of performing act 240, the current set and the proposed set of model parameter estimates are fused to form a fused set of model parameter estimates that may operate as the final set of model parameter estimates or may operate as a new current set of model parameter estimates for a next iteration. To determine whether to use the fused set of model parameter estimates as the final set or to iterate, the fused set of model parameters are evaluated to ascertain whether they satisfy one or more criteria (act 250). For example, the fused set of model parameters may be evaluated to determine whether the changes to the model parameter estimates and/or the rate of change of the model parameter estimates is below a predetermined threshold. When changes and/or rate of change becomes sufficiently small, the fused set of model parameter estimates may be considered to have converged suitably such that the fused set of model parameter estimates are deemed accurate characterizations of the DW-MRI data.

In implementations that employ an energy optimization scheme, evaluating the one or more criteria may include assessing whether the energy reduction achieved in the respective iteration is below a threshold, and if so, the fused set of model parameter estimates may be considered to have suitably converged. However, any suitable criteria may be used to evaluate whether the fused set of model parameter estimates provide a satisfactory fit to the DW-MRI data, or whether further iterations should be performed.

When the fused set of model parameter estimates satisfy the one or more criteria, the fused set of model parameter estimates may be accepted as the final model parameter estimates for the DW-MRI data (act 260). If the fused set of model parameter estimates does not satisfy the one or more criteria, the fused set of model parameter estimates may be used as a new current set of model parameter estimates and acts 230-250 may be repeated until the resulting fused set of model parameter estimates satisfy the one or more criteria. The approach described in method 200 above facilitates iteratively adjusting model parameter estimates until an acceptably optimal set of model parameter estimates are found. However, other techniques may be utilized alternatively or in addition to method 200 described in the foregoing. Specific examples of techniques suitable for implementing method 200, some of which were discussed in the foregoing, are described in further detail below.

As discussed above, some embodiments employ a new model of DW-MRI signal decay that accounts for both inter-voxel and intra-voxel incoherent motion of the water molecules. This incoherent motion (IM) model may be achieved in part by introducing spatial homogeneity to the conventional IVIM model of DW-MRI signal decay. According to some embodiments, estimates of IM model parameters for all voxels are produced simultaneously, rather than solving for each voxel independently as is done using some conventional techniques. As a result, the reliability of the incoherent motion parameter estimates from the DW-MRI data may be increased without acquiring additional data and/or losing spatial sensitivity.

Introducing spatial homogeneity may be achieved via Bayesian estimation of Markov Random Field (MRF) models having spatial homogeneity as a prior term, thus accounting for at least some inter-voxel interactions. The inventors have appreciated that the optimization of MRF-related energy functions is challenging due, at least in part, to the relatively large number of variables that must be optimized simultaneously, especially when compared to the relatively fewer number of variables that are optimized with conventional independent voxel-wise approaches. To address such optimization challenges, the inventors have developed an iterative approach, an example of which was discussed above in connection method 200 illustrated in FIG. 2. An example implementation of this method is described below in connection with a "fusion bootstrap moves" (FBM) solver to iteratively generate parameter estimates for the new IM model that account for inter-voxel interactions (e.g., by enforcing a measure of spatial homogeneity).

According to some embodiments, the FBM solver iteratively updates parameter estimates by applying a binary graph-cut solver to fuse a current set of IM model parameters with a proposal set of IM model parameter estimates to obtain a fused set of IM model parameter estimates that better fit the observed DW-MRI data. The proposals of parameter values may be sampled from the independent voxel-wise distributions of the parameters values with a model-based bootstrap resampling of the residuals, as discussed in further detail below (the stochastic perturbation discussed above is one exemplary method for doing so). An example of a standard formulation of an IVIM model of DW-MRI signal decay assumes a signal decay function of the form:

$$m_{v,i} = s_{0,v}(f_v \exp(-b_i(D^*_v + D_v)) + ((1 - f_v)(\exp(-b_i D_v)))) \quad (1).$$

In the expression in equation 1; $m_{i,v}$ is the expected signal of voxel v at b-value i; $b_i$, $s_{0,v}$ is the baseline signal at voxel v; $D_v$ is the slow diffusion decay associated with extravascular water molecules' motion, $D^*_v$ is the fast diffusion decay associated with the intravascular water molecules' motion; and $f_v$ is the fraction between the slow and fast diffusion compartments. Given the DW-MRI data acquired with multiple b-values, the observed signal ($S_v$) at each voxel v is a vector of the observed signal at the different b-values: $S_v = \{s_{v,i}\}$, i=1 ... N. The IVIM model parameters at each voxel v may be modeled as a continuous-valued four-dimensional random variable $\Theta_v$ (i.e. $\Theta_v = \{s_{0,v}, f_v, D^*_v, D_v\}$). The IVIM model parameters $\Theta_v$ may be estimated from the DW-MRI signal $S_v$ using an independent voxel-wise maximum-likelihood estimator:

$$\hat{\theta}_v = \underset{\theta_v}{\mathrm{argmax}}\, p(s_v \mid \theta_v) = \underset{\theta_v}{\mathrm{argmax}} \prod_{i=1}^{N} p(s_{v,i} \mid \theta_v). \quad (2)$$

As discussed in further detail below, acquiring DW-MRI data may be performed, at least in part, using parallel MRI image acquisition techniques. Assuming a non-central $\chi$-distribution noise model for parallel MRI acquisition as used in DW-MRI, $p(s_{v,i} \mid \Theta_v)$ takes the following form:

$$p(s_{v,i} \mid \theta_v) = \frac{s_{v,i}}{\sigma^2}\left(\frac{m_{v,i}}{s_{v,i}}\right)^{k-1} \exp\left(-\frac{s_{v,i}^2 + m_{v,i}^2}{2\sigma^2}\right) I_{k-1}\left(\frac{s_{v,i} m_{v,i}}{\sigma}\right). \quad (3)$$

In the expression in equation 3, a represents the noise standard deviation of the Gaussian noises present on each of the acquisition channels, k represents the number of channels used in the acquisition, and $I_{k-1}$ represents the $(k-1)^{th}$ order modified Bessel function of the first kind. Using a Gaussian approximation of the non-central $\chi$-distribution and taking the negative log of the maximum likelihood estimator, the maximum likelihood estimation takes the form of a least-squares minimization problem:

$$\hat{\theta}_v = \underset{\theta_v}{\mathrm{argmin}} \sum_{i=1}^{N} (m_{v,i} - s_{v,i})^2. \quad (4)$$

The IVIM model parameters $\Theta_v$ may be estimated from the DW-MRI signal $S_v$ by solving the least-squares minimization problem expressed above in equation 4 independently for each voxel using any suitable optimization algorithm. However, it should be appreciated that solving the above equation independently for each voxel accounts for intra-voxel interactions, but does not account for inter-voxel interactions. As discussed above, a spatial homogeneity constraint may be utilize to account for at least some inter-voxel interactions. According to some embodiments, a Bayesian framework is employed and inter-voxel interactions may be accounted for, at least in part, using a spatial homogeneity prior. From this Bayesian perspective, the IVIM model parameters $\Theta$ (also referred to as parametric maps) that maximize the posterior probability associated with the parametric maps given the observed signal S and the spatial homogeneity prior knowledge may be found as follows:

$$\hat{\theta} = \underset{\theta}{\mathrm{argmax}}\, p(\theta \mid S) \propto p(S \mid \theta) p(\theta). \quad (5)$$

By using a spatial prior in the form of a continuous-valued Markov random field, the posterior probability $p(S|\Theta)p(\Theta))$ can be decomposed into the product of node and clique potentials:

$$p(S \mid \theta) p(\theta) = \prod_v p(S_v \mid \theta_v) \prod_{v_p \sim v_q} p(\theta_{v_p}, \theta_{v_q}). \quad (6)$$

In the expression above in equation 6; $p(\Theta_v|S_v)$ is the data term representing the probability of voxel v having the DW-MRI signal $S_v$ given the model parameters $\Theta_v$; $v_p \sim v_q$ is the collection of the neighboring voxels according to the employed neighborhood system; and $p(\Theta_{vp}, \Theta_{vq})$ is the spatial homogeneity prior in the model. It should be appreciated that the neighboring voxels may be chosen in any desired way including adjacency, defining a predetermined neighborhood or using a data driven approach based on the DW-MRI data. By taking the negative logarithm of the posterior probability in equation (6), the maximum a posteriori (MAP) estimate $\Theta$ is equivalent to the minimization of:

$$E(\theta) = \sum_v \varphi(S_v, \theta_v) + \sum_{v_p \sim v_q} \psi(\theta_{v_p}, \theta_{v_q}). \quad (7)$$

In the expression of equation 7, $\phi(S_v, \Theta_v)$ and $\psi(\Theta_{vp}, \Theta_{vq})$ are the compatibility functions:

$$\phi(S_v, \Theta_v) = -\log p(S_v \mid \theta_v)$$

$$\psi(\theta_{v_p}, \theta_{v_q}) = -\log p(\theta_{v_p}, \theta_{v_q}) \quad (8).$$

The data term $\phi(S_v, \Theta_v)$ is given by taking the negative logarithm of equation 3 and the spatial homogeneity term is defined using the robust L1-norm:

$$\psi(\theta_{v_p}, \theta_{v_q}) = \alpha W |\theta_{v_p} - \theta_{v_q}| \quad (9)$$

In the expression of equation 9, $\alpha \geq 0$ weights the amount of spatial homogeneity enforced by the model, and W is a diagonal weighting matrix that accounts for the different scales of the parameters in $\Theta_v$. The very high dimensionality of the parameters' vector $\Theta$ of the energy function in equation 7 (e.g., the number of voxels in the image multiplied by the number of the signal decay model parameters) makes energy optimization very challenging. The inventors have developed an iterative algorithm referred to above as the FBM solver to robustly minimize the energy in equation 7.

Some embodiments utilize a combinatorial binary graph-cut approach to address at least some of the challenges associated with continuous MRF optimization. As discussed above in connection with the method 200 illustrated in FIG. 2, parameter estimates may be obtained iteratively by stochastically perturbing a current set of model parameter estimates to obtain a proposed set of model parameter estimates and fusing the current set and the proposed set (and potentially repeating) until the fused set of model parameter estimates meet one or more criteria. According to some embodiments, fusing may be performed using a binary graph-cut solver to fuse the current set of model parameter estimates with the proposal set of model parameter estimates to obtain a fused set of model parameter estimates that better fit the observed DW-MRI data. The proposals of parameter values may be sampled from the independent voxel-wise distributions of the parameters values with a model-based bootstrap resampling of the residuals.

Using a binary graph-cut solver, as described in further detail below, may allow the fusion of the current set of model parameter estimates and the proposal set of model parameter estimates (e.g., obtained by stochastically perturbing the current set of model parameter estimates) to be optimal at each iteration. As a result, reduction in the overall model energy in equation 7 may be guaranteed in this respect. By stochastically perturbing and fusing iteratively (e.g., as described above in connection with method 200 illustrated in FIG. 2), the algorithm can robustly converge, at least to a local minimum. As a result, the IM model parameters may be estimated accurately and precisely.

Examples of perturbing the current set of model parameter estimates to obtain a proposal set of model parameter estimates (also referred to as proposal drawing due to the fact that a new proposal for the model parameter estimates are being drawn from the current set via stochastic perturbation) and fusing the current set and the proposal set, in accordance with some embodiments, are discussed in further detail below.

To obtain a proposal set of IM model parameter estimates, a model-based bootstrap technique may be utilized to draw a new proposal from the empirical distribution of the incoherent motion parameter values. For example, for each voxel v, the raw residuals between the observed signal ($S_v$) at voxel v and the expected signal ($M_v = \{m_{v,i}\}$, $i=1, \ldots N$) at each b-value $b_i$, given the current model estimate ($\Theta^0_v$), may be defined as:

$$\epsilon_{v,i} = s_{v,i} - m_{v,i} \quad (10)$$

The model-based bootstrap resampling may be defined as:

$$s^*_{v,i}(\theta^0_v) = m_{v,i} + t_{v,i} \hat{\epsilon}_{v,i} \quad (11)$$

In the expression in equation 11; $s^*_{v,i}(\Theta^0_v)$ is the resampled measures at b-value $b_i^*$, $i=1 \ldots N$, $\hat{\epsilon}_{v,i}$ are the rescaled version of $\hat{\epsilon}_{v,i}$ that accounts for heterogeneous errors leverages; and $t_{v,i}$ is a two-point Rademacher distributed random variable with $P(t_{v,i}=1)=0.5$ and $p(t_{v,i}=-1)=0.5$ defined for each voxel and b-value independently. That is, the model parameter estimates at each voxel are stochastically perturbed by randomly either adding to or subtracting from the current model parameter estimates an amount $\hat{\epsilon}_{v,i}$ based on the residuals between the observed and expected DW-MRI data. The new proposal of the IVIM model parameters $\Theta^1_v$ may then be estimated for each voxel independently using equation 4.

The inventors have appreciated that simply drawing samples from a pre-defined artificial distribution of the parameters may not be appropriate as the actual distribution of the parameters is spatially variant. Therefore, samples drawn from a pre-defined artificial distribution will generally slow the optimization as such samples have a greater chance of being rejected by the optimization, for example, the graph-cut optimization described below. As such, samples may be drawn from the spatially-variant distribution using the bootstrap process described herein.

As discussed above, the inventors have recognized that a binary graph-cut technique may be employed to find the optimal fusion of the current assignment $\Theta^0$ (i.e., the current set of model parameter estimates) and the new proposal $\Theta^1$ (i.e., the proposal set of model parameter estimates) for the IM model parameter values that form a new estimate of the parameter maps $\Theta^0$ (i.e., a fused set of model parameter estimates) which have a minimal energy in an optimization respect among the possible fusions of $\Theta^0$ and $\Theta^1$. One example implementation is as follows:

Let G=(V, E) be an undirected graph where each voxel v is represented as a graph node, the two proposals $\Theta^0$ and $\Theta^1$ are represented by the terminal nodes $v_s$ and $v_t$, and graph edges consist of three groups: $E = \{(v_p, v_q), (v_p, v_s), (v_p, v_t)\}$. Edge weights $w(v_p, v_s)$ and $w(v_p, v_t)$ represent the likelihood of the model parameters $\Theta^0$ and $\Theta^1$ given the observed signal $S_{v_p}$, respectively, as expressed by the following:

$$w(v_p, v_s) = \phi(S_v; \Theta^0_v), w(v_p, v_t) = \phi(S_v; \Theta^1_v) \quad (12).$$

Edge weights $w(v_p, v_q)$ penalize for adjacent voxels that have different model parameters:

$$w(v_p, v_q) = \psi(\Theta v_p, \Theta v_q) \quad (13).$$

Accordingly, penalizing differences in model parameters for adjacent voxels (and/or neighborhood voxels) enforces a spatial homogeneity constraint on the fusion operation and, as a result, at least some inter-voxel interactions may be accounted for in the selection of optimal model parameter estimates. The optimal fusion between $\Theta^0$ and $\Theta^1$ forming the new estimate of the parameter maps $\Theta^*$ (i.e., the fused set of model parameter estimates) may be found by solving the corresponding graph min-cut problem. An example of solving the graph min-cut problem is described in Lempitsky, V., et al, *Fusion moves for Markov random field optimization*, IEEE Trans Pattern Anal Mach Intell, 2010. 32 (8): p. 1392-1405. The resulting fused set of model parameter estimates $\Theta^*$ may be assigned as $\Theta^0$ for the next iteration. The above described process of stochastically perturbing and fusing may be repeated until the fused set of model parameter estimates meet one or more criteria that, for example, reflect that the set of model parameter estimates have substantially converged and/or are otherwise satisfactory for use as the final set of model parameter estimates.

Figure 3:
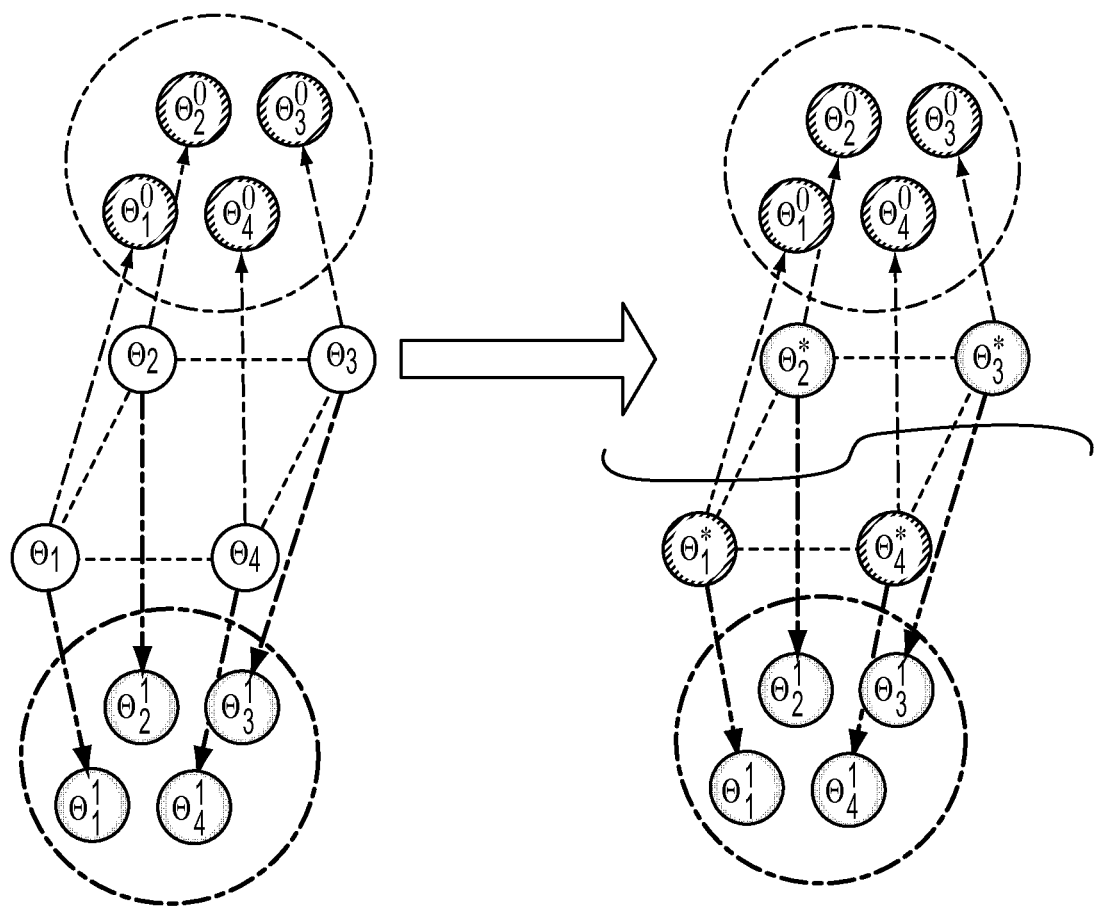
FIG. 3 schematically illustrates fusing current and proposal model parameter estimates, in accordance with some embodiments.

FIG. 3 depicts schematically the operation performed on a portion of a graph set-up for the minimization of energy in equation 7. In particular, in the example illustrated in FIG. 3, $\Theta^0$ represents a current set of model parameter estimates and $\Theta^1$ represents a proposal set of model parameter estimates for the four adjacent voxels illustrated. In this schematic example, the graph min-cut algorithm selected current model parameter estimates for voxels 1 and 4 and proposal model parameter estimates for voxels 2 and 3 to form the fused set of model parameter estimates for the exemplary four voxels as a better fit to the observed DW-MRI data respecting the spatial homogeneity constraint (e.g., by minimizing the energy in equation 7 according to the graph min-cut algorithm). The fused set of model parameter estimates may form the basis of the next iteration or may represent a final set of model parameter estimates based on evaluating the fused set of model parameters according to one or more criteria. For example, the reduction in energy resulting from the fusion may be evaluated to determine when to stop iterating and accept the fused set of model parameter estimates.

Aspects of the above described FBM approach have the advantage that the approach need not assume any specific noise model in estimating the distribution of residuals and can therefore accommodate both acquisition noise and motion-related artifacts. According to some embodiments, the approach does not require the calculation of derivatives and therefore can be coupled directly with robust spatial priors including the L1-norm. While the above described FBM method is described above to optimize a Bayesian model of incoherent motion from DW-MRI data, the FBM techniques may be applied to other parametric MRI reconstruction problems as well, including to facilitate the estimation of kinetic parameters from DCE-MRI and quantitative T1 from T1-weighted MRI, for example.

Figure 4:
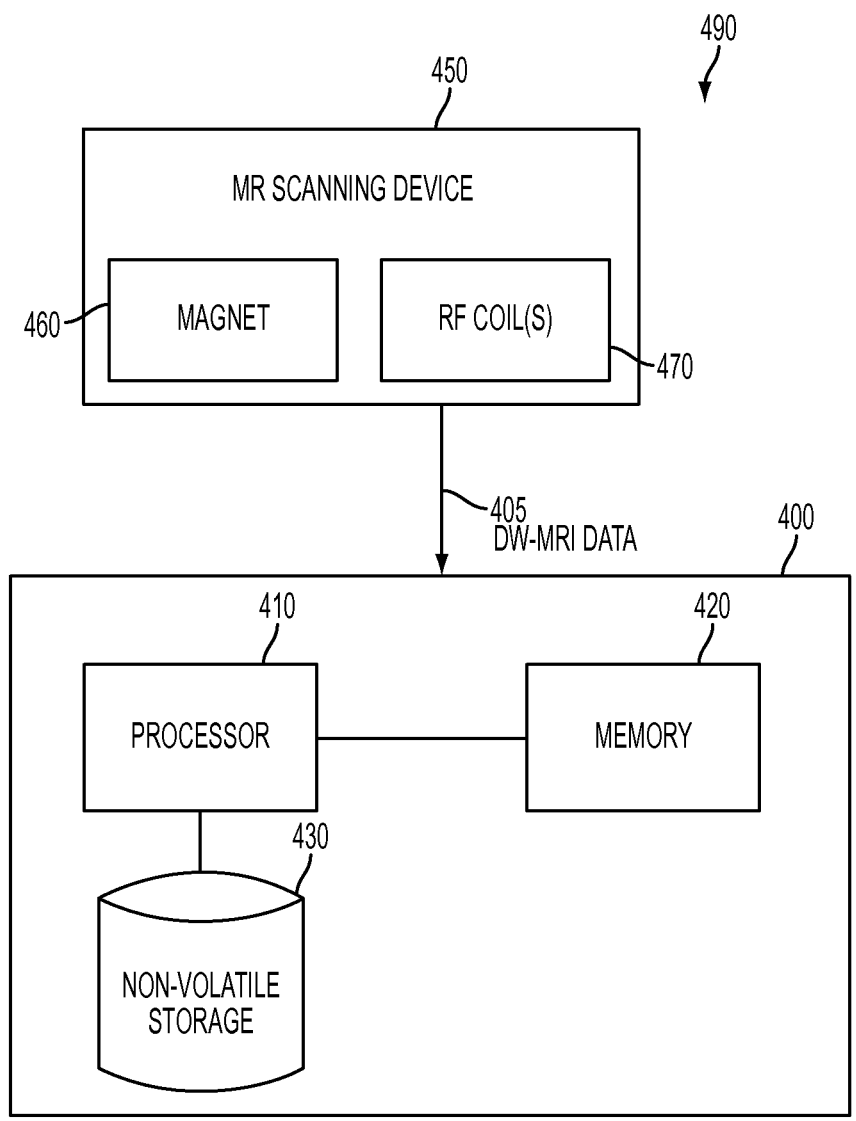
FIG. 4 illustrates a MR scanning device suitable for obtaining DW-MRI data and a computer system suitable for implementing model parameter estimation techniques described herein.

FIG. 4 illustrates a block diagram of one embodiment of a system 490 suitable for practicing various techniques described herein. System 490 comprises a magnetic resonance (MR) scanning device 450 and computer system 400. MR scanning device 450 may be any device capable of obtaining MR data and, in particular, capable of acquiring DW-MRI data. For example, MR scanning device 450 may include a magnet 460 capable of producing a magnetic field of desired strength, and may produce a uniform or gradient magnetic field. Magnet 460 may be of any shape, size and strength and may include multiple magnets of any size, shape and strength.

MR scanning device 450 also comprises one or more RF coils 470 arranged proximate the magnet and adapted to provide RF pulse sequences to an object being scanned and/or to detect NMR signals (e.g., DW-MRI signals) emitted therefrom. RF coils 470 may comprise one or multiple coils arranged in any configuration to perform single coil acquisition or multiple coil acquisition (i.e., parallel MR). RF coils 470 may include independent RF coils for providing RF pulse sequences (excitation coils) and detecting NMR signals (receive coils), or one or more RF coils may be arranged as both an excitation and receive coils. Any configuration of magnet 460 and RF coil(s) 470 may be suitable, as the techniques described herein are not limited for use on data obtained from any particular MR scanning device.

Computer system 400 may be used to implement one or more techniques described herein. Computer system 400 may include one or more processors 410 and one or more non-transitory computer-readable storage media (e.g., memory 420 and one or more non-volatile storage media 430). The processor 410 may control writing data to and reading data from the memory 420 and the non-volatile storage device 430 in any suitable manner Processor 410, for example, may be a processor on any device, for example, a personal computer, a workstation, one or more servers, or may be a processor on-board or otherwise integrated with MR scanning device 450, etc.

To perform functionality and/or techniques described herein, the processor(s) 410 may execute one or more instructions stored in one or more computer-readable storage media (e.g., the memory 420, storage media, etc.), which may serve as non-transitory computer-readable storage media storing instructions for execution by processor(s) 410. Computer system 400 may also include any other processor, controller, or control unit needed to route data, perform computations, perform I/O functionality, etc. For example, computer system 400 may include any number and type of input functionality to receive data and/or may include any number and type of output functionality to provide data, and may include control apparatus to perform I/O functionality.

Computer system 400 may be integrated into MR scanning device 450 or may be a separate stand-alone computer system, either proximate to or remote from MR scanning device 450. For example, computer system 400 may be connected to MR scanning device 450 over a network, connected to multiple scanning devices or may not be connected to any scanning device at all. When computer system 400 is connected to or integrated with MR scanning device 450, computer system 400 may be programmed to control the RF coil(s) according to a desired RF sequence or protocol, or MR scanning device 450 may have a separate controller to perform excitation and acquisition.

When computer system 400 is separate from MR scanning device 450, computer system 400 may operate on MR data (e.g., DW-MRI data) previously stored on computer system 400, may obtain DW-MRI data from some other location, e.g., another computer system, over a network, or may obtain the DW-MRI data via transportable storage medium, etc. It should be appreciated that any computing environment may be used, as the techniques described herein are not limited for use with a computer system of any particular type or implementation.

The terms "program" or "software" are used herein in a generic sense to refer to any type of computer code or set of processor-executable instructions that can be employed to program a computer or other processor to implement various aspects of embodiments as discussed above (e.g., to implement one or more parameter estimate techniques described herein). Additionally, it should be appreciated that according to one aspect, one or more computer programs that when executed perform one or more techniques described herein need not reside on a single computer or processor, but may be distributed in a modular fashion among different computers or processors to implement various aspects of the techniques described.

Processor-executable instructions may be in many forms, such as program modules, executed by one or more computers or other devices. Generally, program modules include routines, programs, objects, components, data structures, etc. that perform particular tasks or implement particular abstract data types. Typically, the functionality of the program modules may be combined or distributed as desired in various embodiments.

Also, data structures may be stored in one or more non-transitory computer-readable storage media in any suitable form. For simplicity of illustration, data structures may be shown to have fields that are related through location in the data structure. Such relationships may likewise be achieved by assigning storage for the fields with locations in a non-transitory computer-readable medium that convey relationship between the fields. However, any suitable mechanism may be used to establish relationships among information in fields of a data structure, including through the use of pointers, tags or other mechanisms that establish relationships among data elements.

Also, various inventive concepts may be embodied as one or more processes, such as process 200 described with reference to FIG. 2. The acts performed as part of each process may be ordered in any suitable way. Accordingly, embodiments may be constructed in which acts are performed in an order different than illustrated, which may include performing some acts concurrently, even though shown as sequential acts in illustrative embodiments.

Using techniques describe herein, and in particular, techniques associated with improving IM model parameter estimates, improvements in diagnostic procedures may be achieved, for example, improvements in the characterization of heterogeneous tumor environments, among other diagnostic procedures. To quantify at least some improvements, techniques described herein in connection with the IM model and the FBM solver were compared with the conventional IVIM model approach. Experiments were performed using simulated data and in-vivo abdominal DW-MRI data of 30 patients, and in-vivo DW-MRI data of three patients with musculoskeletal lesions.

Using aspects of the IM model with the FBM solver described above for inference a reduction of the relative root mean square error of the D* parameter estimates by 80% and of the f, and D parameter estimates by 50% compared to the conventional IVIM model on the simulated data was achieved. Similarly, using aspects of the disclosed IM model with the FBM solver for inference also reduced the coefficient of variation of parameter estimates of the D* parameter by 43%, the f parameter by 37%, and the D parameter by 17%, compared to the conventional IVIM model (paired Student's t-test, $p<0.0001$).

In addition, using aspects of the IM model with the FBM solver described herein for inference improved the characterization of heterogeneous musculoskeletal lesions by means of increased contrast-to-noise ratio by 19.3% compared to the conventional IVIM model. As such, aspects of the IM model with the FBM solver are capable of facilitating more precise insight into the physiological causes of the DW-MRI signal decay and a better mechanism to characterize heterogeneous lesions than the conventional IVIM model, which not only generally produces less accurate model parameter estimates but does not account for inter-voxel interactions.

Provide below is a description of the methodology used to compare aspects of the IM model and FBM solver described herein with the conventional IVIM model approach on the simulated DW-MRI data and the in-vivo DW-MRI that resulted in the improvements summarized above. The below described methodology is provided to illustrate improvement that may be achieved, but the particular experiments performed do not limit the invention in any, as the techniques described herein may be applied in any suitable DW-MRI environment to facilitate estimating IM model parameters of DW-MRI data obtained from any portion or portions of the physiology, and the applications of the techniques described herein are not limited to the applications described below, nor are they limited to any particular application.

In the exemplary experiments described herein, the spatial homogeneity prior model defines three hyper-parameters: 1) the standard deviation of the signal noise; 2) the parameter weighting matrix W; and 3) the spatial smoothness prior weight a. The standard deviation of the signal noise may be estimated from a pre-defined background region for each dataset. The impact of spatial smoothness prior weight a on the simulated data as well as on preliminary in-vivo DW-MRI data of healthy subjects was assessed and the value of a was set to 0.01 for the following experiments. We used this value in all of the DW-MRI data analyses presented in this manuscript.

The first experiments performed involved simulated DW-MRI data. For these experiments, a Monte-Carlo simulation study to analyze the estimation errors in incoherent motion quantification from DW-MRI using the conventional IVIM model techniques and using aspects of the IM model with the spatial homogeneity prior was conducted. To assess the efficacy of aspects of the FBM solver, the graph min-cut based fusion described above was compared against two versions of a conventional ICM algorithm: 1) a continuous ICM in which energy minimization is performed for each voxel on the continuous domain with the current estimate of the incoherent motion parameters of the neighboring voxels as constraints with a derivative-free non-linear optimization algorithm; and 2) a discrete version in which the ICM strategy is used to reach an approximate solution for each fusion problem, but otherwise leaving the entire fusion framework unchanged.

Figure 5A:
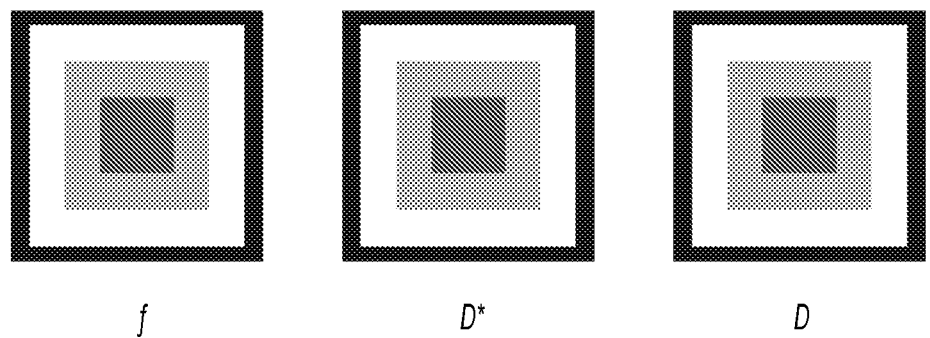
FIG. 5A depicts reference parameter maps of f, D* and D for an experiment using simulated DW-MRI data.
Figure 5B:
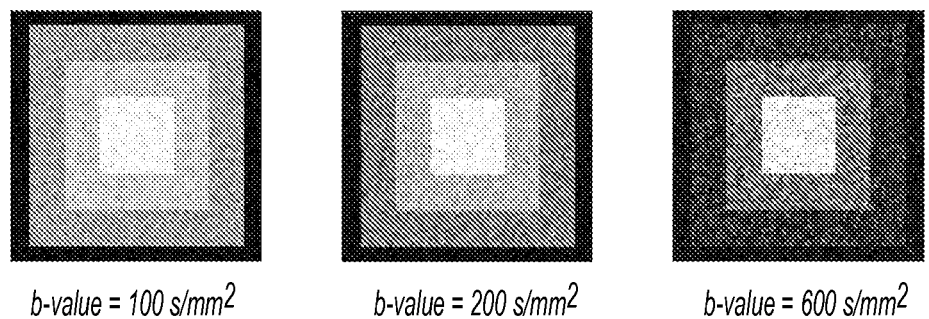
FIG. 5B depicts simulated noisy DW-MRI images with different b-values generated using the reference parameter maps in FIG. 5A that were utilized in simulated data experiments.

A simulated heterogeneous tumor example was constructed as follows. Three-dimensional reference parametric maps with 100×100×5 voxels were defined with the following parameters: Border: $\Theta=\{200, 0.35, 0.03, 0.003\}$, middle part: $\Theta=\{200, 0.25, 0.02, 0.002\}$, innermost part: $\Theta=\{200, 0.15, 0.01, 0.001\}$. Simulated DW-MRI images from the parametric maps using equation 1 with seven b-values in the range [0, 800] s/mm$^2$ were computed. The simulated data was then corrupted by non-centralized $\chi$-distributed noise with single coil noise $\sigma$ values in the range of 2-16 defined on the same scale as the assumed $s_0$, which implies an assumed SNR range of 100-12.5 db. FIG. 5A depicts reference parameter maps of f, D* and D and FIG. 5B depicts simulated noisy DW-MRI images with different b-values generated using the reference parameter maps in FIG. 5A that were utilized in the simulated data experiments.

The model parameters $\Theta$ were estimated from the noisy DW-MRI data for each voxel using the following four methods: 1) the conventional voxel-independent IVIM approach (IVIM in the results below); 2) the inventors' IM model using a spatial homogeneity prior model, with ICM based continuous optimization (IM-ICM); 3) the inventors' IM model using a spatial homogeneity prior model, with ICM fusion strategy (IM-ICM$_D$), and; 4) the inventors' IM model using a spatial homogeneity prior model, with the inventors' graph min-cut fusion strategy (IM-FBM). The noise parameter $\sigma$ was estimated using a pre-defined background region. Stopping criteria for all methods (IM-ICM$_C$, IM-ICM$_D$, IM-FBM) was defined as an energy improvement of less than 0.1% from the initial energy or 500 iterations. The estimator bias, the standard deviation and the relative root mean square (RRMS) error between the reference and estimated parameters for each parameter was calculated and the increase in computation time (due to the Bayesian model estimation) in both the FBM and the ICM approaches to the computation time of the independent voxel-wise IVIM approach were compared.

Figure 6:
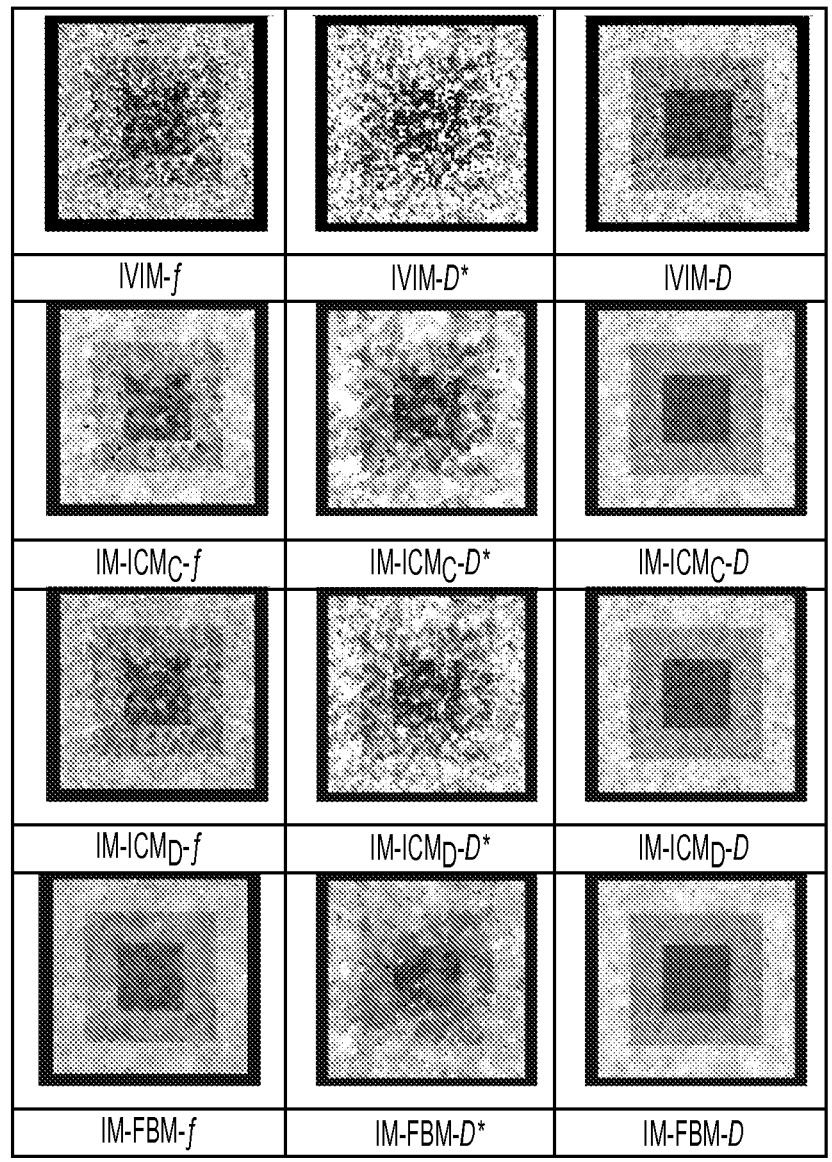
FIG. 6 depicts parametric maps estimated from simulated DW-MRI data using a conventional IVIM approach and using exemplary incoherent motion (IM) model parameter estimation techniques described herein.

FIG. 6 depicts the parametric maps estimated from the simulated DW-MRI data using the conventional IVIM approach as well as the inventors' IM model Bayesian with spatial homogeneity prior optimized using: 1) the continuous ICM method (IM-ICM); 2) the discrete ICM method (IM-ICM$_D$); and 3) the inventors' FBM method (IM-FBM). In particular, the first row depicts the incoherent motion parametric maps (f D*, and D) calculated using the conventional IVIM approach, the second row depicts the maps calculated using the IM-ICM$_C$ approach, the third row depicts the maps calculated using the IM-ICM$_D$ approach, and the fourth row depicts the maps calculated using the IM-FBM approach. The results evidence that the inventors' IM model with spatial homogeneity prior yields smoother, more realistic maps than does the conventional IVIM approach ($1^{st}$ row). In addition, the FBM optimizer ($4^{th}$ row) yield smoother maps with more accurate structure compared to the two versions of the ICM optimizer ($2^{nd}$ and $3^{rd}$ rows), especially with respect to the f parameter.

Figure 7:
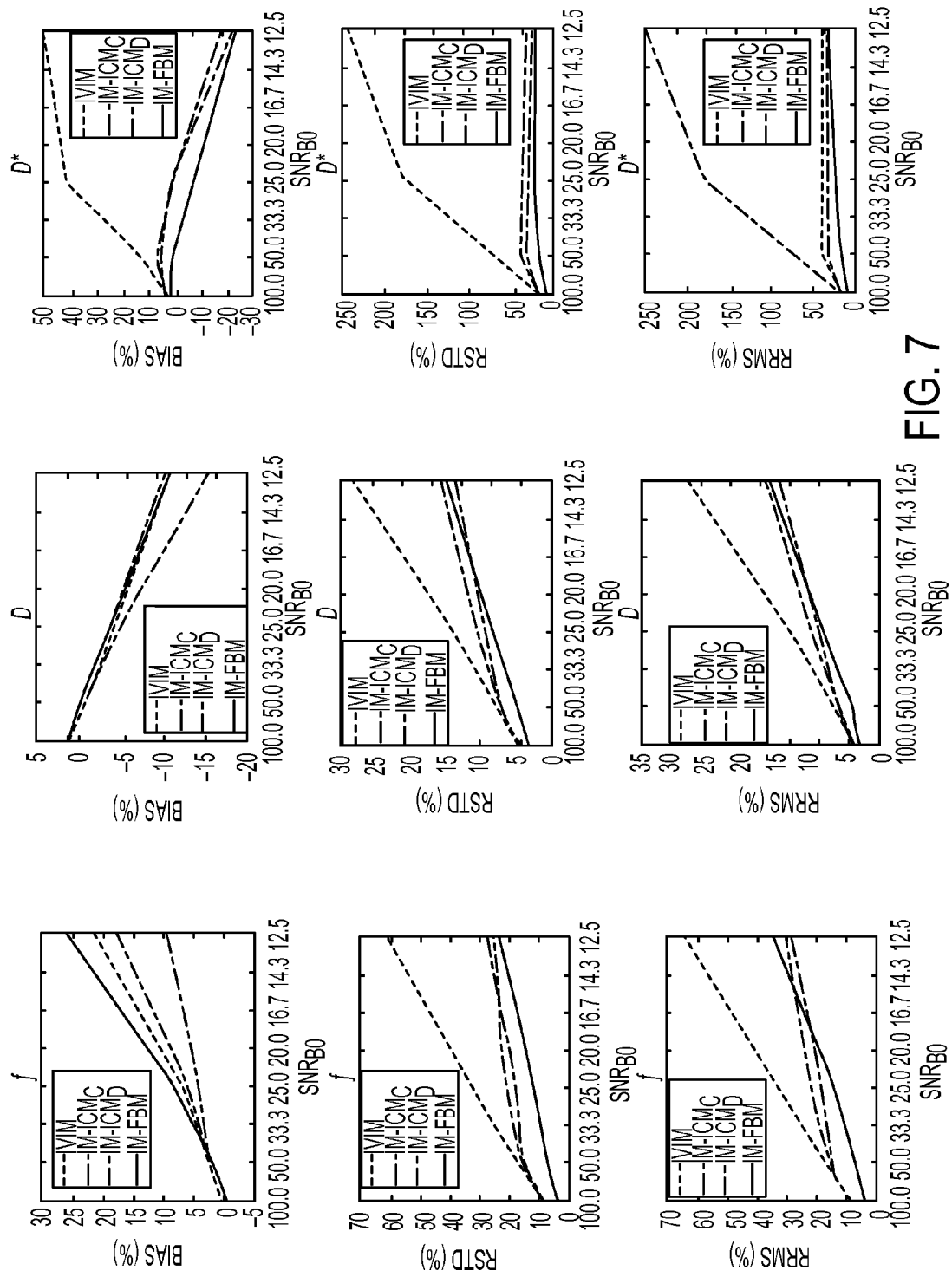
FIG. 7 shows plots of the relative bias, the relative standard deviation of the estimates error, and the RRMS plots of the incoherent motion parameter estimators as a function of the SNR using a conventional IVIM approach and using exemplary incoherent motion (IM) model parameter estimation techniques described herein.

FIG. 7 presents the relative bias, the relative, standard deviation of the estimates error, and the RRMS plots of the incoherent motion parameter estimators as a function of the SNR using the conventional IVIM approach as well as the inventors IM model with spatial homogeneity prior, that were then optimized using the ICM$_C$, the ICM$_D$, and the inventors' FBM methods. In particular, the first row depicts the bias of each of the estimators used to estimate the incoherent motion model parameters (i.e., IVIM, IM-ICM$_C$, IM-ICM$_D$, and IM-FBM), the second row depicts the precision of each estimator by means of the relative standard deviation of the estimate errors, and the third row depicts the overall RRMS of each estimator. As shown, the introduction of the spatial homogeneity prior improved both the accuracy and precision of the parameter estimates. Under a realistic SNR$_{BO}$ scenario of 20 db, the inventors IM-FBM approach yielded the most precise estimates for all parameters.

The greatest improvement were observed in the bias of the estimates in the D* parameter where the bias was reduced from ~40% with the conventional IVIM method to 10% using the IM-FBM method, and to ~5% using the IM-ICM$_C$ and IM-ICM$_D$ methods in realistic SNR$_{BO}$ of 20 db. Using the IM-FBM approach, the greatest improvement in the precision of the estimates was achieved where the relative, standard deviation of the estimates error and overall RRMS was reduced by 80% for the D* parameter; and by 50% for the D and f parameters, compared to the conventional IVIM approach in a realistic SNR$_{BO}$ scenario of 20 db.

The computation time required to reconstruct the parametric maps of one slice of 100×100 voxels on a single processor machine Intel® Xeon® at 2.40 GHz with cache size of 12 mb were as follows: 1.372 sec for the entire slice (0.137 ms per voxel) using the IVIM approach; 52.9 sec for the entire slice (5.29 ms per voxel) using the IM-ICM$_C$ approach; 112.8 sec for the entire slice (11.28 ms per voxel) using the IM-ICM$_D$ approach; and 142.12 sec for the entire slice (14.21 ms per voxel) using the IM-FBM approach.

The second experiments performed involved in-vivo data. In particular, DW-MRI images of 30 subjects—18 males and 12 females with a mean age of 14.7 (range 5-24, std 4.5) that underwent MRI studies due to suspected inflammatory bowel disease were obtained. Radiological findings of the study subjects' abdominal organs (i.e., liver, kidneys and spleen) were normal. MR imaging studies of the abdomen using a 1.5-T unit (Magnetom Avanto, Siemens Medical Solutions, Erlangen, Germany) with a body-matrix coil and a spine array coil for signal reception were carried out. Free-breathing single-shot echo-planar imaging was performed using the following parameters: repetition time/echo time (TR/TE)=6800/59 ms; SPAIR fat suppression; matrix size=192×156; field of view=300×260 mm; number of excitations=1; slice thickness/gap=5 mm/0.5 mm; 40 axial slices; 8 b-values of 5, 50, 100, 200, 270, 400, 600 and 800 s/mm$^2$. A tetrahedral gradient scheme was used to acquire 4 successive images at each b-value with an overall scan acquisition time of 4 min Diffusion trace-weighted images at each b-value were generated using geometric averages of the images acquired in each diffusion sensitization direction.

Figure 8:
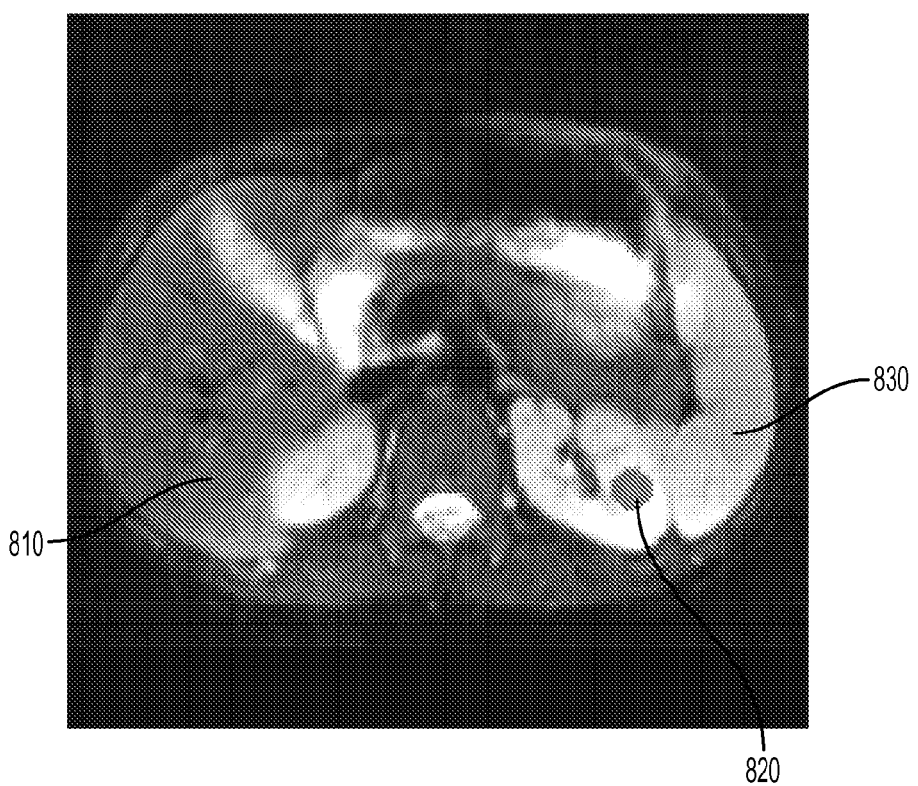
FIG. 8 illustrates an image of the abdomen with the liver, spleen and kidney regions indicated.

The model parameters Θ from the in-vivo DW-MRI data were estimated for each voxel using both the conventional independent voxel-wise approach IVIM and the inventors' IM-FBM approach. The averaged model parameter Θ values obtained using the four different methods over three regions of interest (ROI) were calculated, and each manually annotated in the liver (810 in FIG. 8), the spleen (820 in FIG. 8), and the kidney (830 in FIG. 8). We determined whether there is a statistically significant difference between the average model parameter values estimated with the different estimation methods with a two-tailed, paired Student's t-test, $p<0.05$ indicating a significant difference.

The precision of the parameter estimates were calculated by means of the coefficient of variation (CV) of the parameter estimates at each voxel in the conventional IVIM and the inventors' IM-FBM maps of each patient using model-based wild-bootstrap analysis. For each patient, we averaged the CV values over the same three ROIs mentioned above and illustrated in FIG. 8. The statistical significance of the difference in the precision of the parameter estimates were examined for the conventional IVIM and the inventors' IM-FBM using a two-tailed paired Student's t-test with $p<0.05$ as indicating a significant difference. Heterogeneous musculoskeletal lesions were characterized with the inventors' IM-FBM method in comparison to the conventional IVIM method by means of the contrast-to-noise ratio (CNR) between the lesions components.

DW-MRI data was examined for 3 musculoskeletal lesions patients (2 diagnosed with left femoral osteosarcoma (OS1, OS2), and 1 diagnosed with popliteal cyst (PC) with internal debris in the posterior right calf). The MRI data was acquired using a 3-T unit (Skyra, Siemens Medical Solutions, Erlangen, Germany) DW-MRI protocol was as follows: free-breathing single-shot echo-planar imaging of the lower extremities was performed using the following parameters: repetition time/echo time (TR/TE)=10425/70 ms; SPAR fat suppression; matrix size=128×108; field of view=207×173 mm; number of excitations=5; slice thickness/gap=4 mm/0.0 mm; 40 axial slices; 5 b-values=0, 50, 100, 500 and 800 s/mm$^2$ In addition, post contrast T1-weighted MRI images were acquired.

Figure 9:
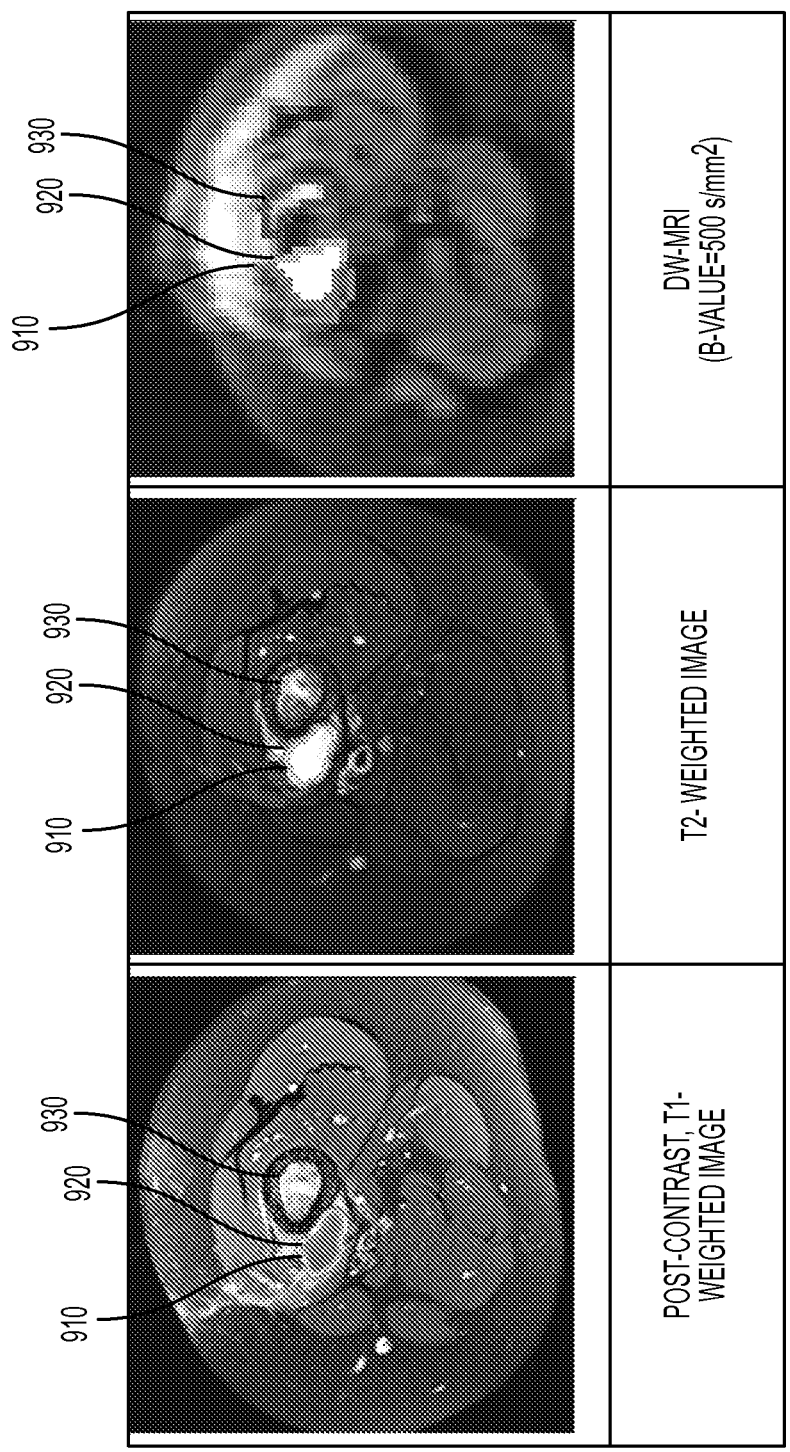
FIG. 9 depicts the left femoral osteosarcoma components on the post-contrast, T1-weighted image, on the T2-weighted image, and on the diffusion-weighted image.

For all cases, an experienced radiologist identified the peripheral rim component and the central part component on the post-contrast, T1-weighted images based on their respective enhancement patterns. FIG. 9 depicts the left femoral osteosarcoma components on the post-contrast, T1-weighted image; on the T2-weighted image; and on the diffusion-weighted image. In FIG. 9, the tumor components are encircled as follows, 910 is peripheral rim of the soft tissue component (Spr), 920 is the central part of the soft-tissue component (Sc), and 930 is the intramedullary component of the tumor.

The incoherent motion parametric maps using the conventional IVIM approach and the inventors' IM-FBM approach were calculated. The internal components, which were annotated manually on the f map, were computed using the IM-FBM approach. The improvement in the contrastto-noise ratio (CNR) was evaluated by looking at the differences in f values among the internal components that resulted from the conventional IVIM and the inventors' IM-FBM approaches, respectively.

Figure 10:
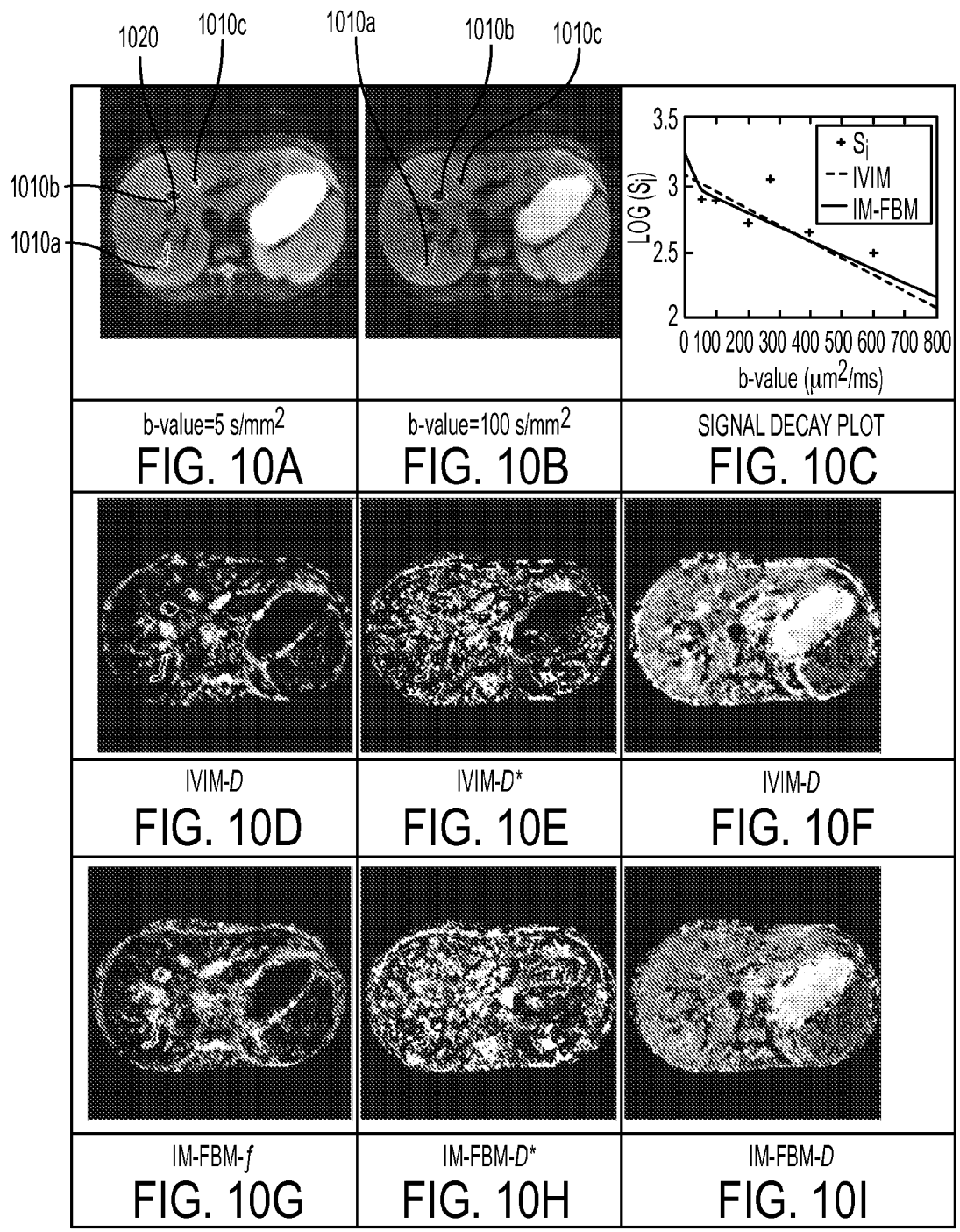
FIG. 10 depicts a representative example of the incoherent motion parametric maps of the upper abdomen calculated using conventional IVIM methods using exemplary incoherent motion (IM) model parameter estimation techniques described herein.

FIG. 10 depicts a representative example of the incoherent motion parametric maps of the upper abdomen calculated using the two methods (i.e., conventional IVIM methods and the inventors IM-FBM approach). In FIG. 10, images (a)-(b) illustrate DW-MRI images with blood vessels inside the liver expected to have labeled as 1010a, 1010b and 1010c. A noisy point inside the liver expected to have a significant percentage of the fast-diffusion component is labeled by voxel 1020 in image (a) in FIG. 10. As illustrated in the signal decay plot of a voxel 1020 in plot (c) in FIG. 10, while the conventional IVIM model failed to depict the fast-diffusion component in the signal decay, the IM-FBM model successfully captured the fast-diffusion component. By incorporating the spatial homogeneity prior, the quality of the images improved (3rd row), compared to the voxel-wise, independent approach ($2^{nd}$ row) that resulted from conventional IVIM. As discussed Table 1 below summarizes incoherent motion model parameters values (mean, std) for each organ as calculated using the conventional IVIM methods and the inventors' IM-FBM techniques.

TABLE 1

|  |  | D | | D* | | f | |
| --- | --- | --- | --- | --- | --- | --- | --- |
|  |  | mean | std | mean | std | mean | std |
| Liver | IVIM | 1.02 | 0.32 | 41.22 | 26.58 | 0.25 | 0.10 |
|  | IM-FBM | 0.95 | 0.26 | 34.43 | 36.22 | 0.28 | 0.10 |
|  | p-value | 0.0011 | | 0.0254 | | <0.001 | |
| Spleen | IVIM | 0.91 | 0.56 | 20.74 | 18.25 | 0.10 | 0.08 |
|  | IM-FBM | 0.82 | 0.37 | 21.04 | 31.44 | 0.13 | 0.09 |
|  | p-value | 0.0297 | | 0.9470 | | 0.0045 | |
| Kidney | IVIM | 1.76 | 0.32 | 23.58 | 26.72 | 0.19 | 0.12 |
|  | IM-FBM | 1.73 | 0.30 | 21.82 | 30.16 | 0.21 | 0.12 |
|  | p-value | 0.0152 | | 0.1371 | | 0.0082 | |

Figure 11:
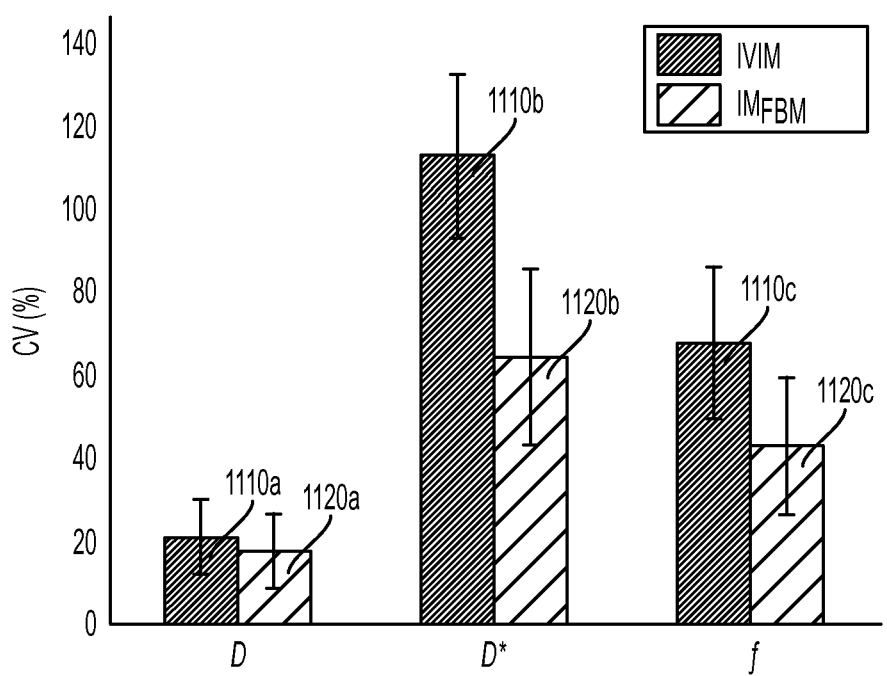
FIG. 11 depicts bar plots of the CV over the 30 subjects for the incoherent motion parameters for a conventional IVIM approach and for exemplary incoherent motion (IM) model parameter estimation techniques described herein.

FIG. 11 depicts the bar plots of the CV over the 30 subjects for the incoherent motion parameters for the conventional IVIM approach (bar labeled 1110a, 1110b and 1110c for the incoherent motion parameters D, D* and f respectively) and for the inventors' IM-FMB approach (bar labeled 1120a, 1120b and 1120c for the incoherent motion parameters D, D* and f respectively). As shown, the CV was significantly lower (p<0.0001) when using the IM-FBM approach than when using the conventional IVIM approach for all parameters. The IM-FBM approach reduced the CV of the D* parameter estimates by 43%, the CV of the f parameter estimates by 37%, and the CV of the D parameter by 17%. The improvement in CV was significant for all parameters (p<0.0001).

Figure 12:
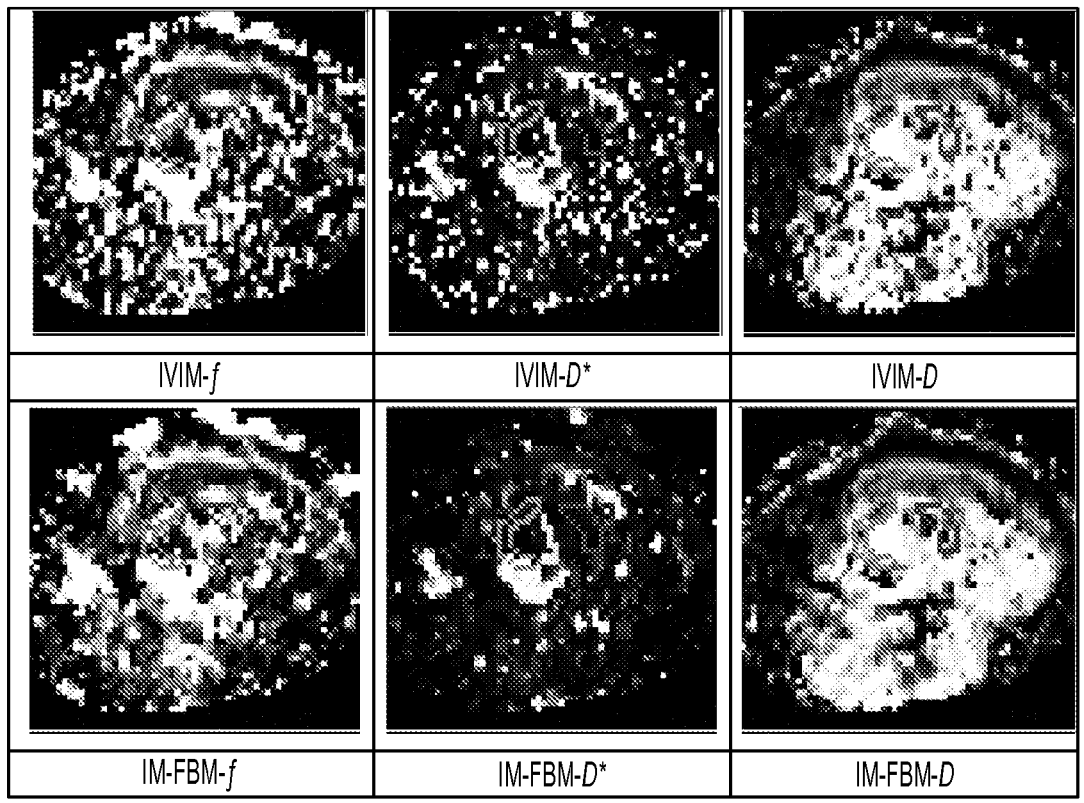
FIG. 12 depicts images of the incoherent motion parametric maps calculated using a conventional IVIM approach and using exemplary incoherent motion (IM) model parameter estimation techniques described herein.

FIG. 12 depicts the incoherent motion parametric maps calculated using the conventional IVIM approach and an IM-FBM approach. The IM-FBM approach produced smoother, more realistic parametric maps with improved sensitivity to details seen especially in the f, and D* maps. In FIG. 12, the incoherent motion parametric maps of the osteosarcoma tumor as calculated using the IVIM approach (first row) and our IM-FBM approach (second row) are shown with the internal tumor components encircled. The IM-FBM approach produced smoother, more realistic maps than did the conventional IVIM approach.

Figure 13:
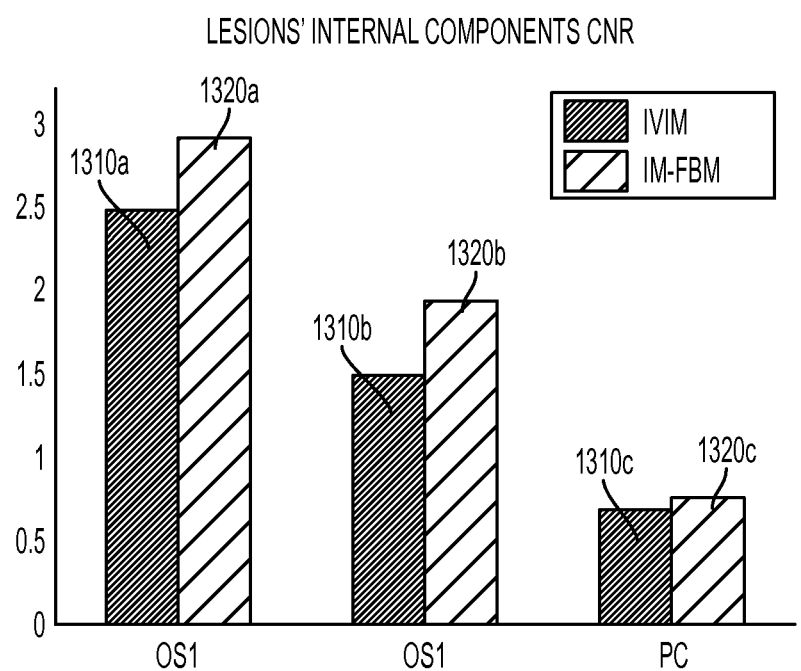
FIG. 13 illustrate bar plots that compare the results of a conventional IVIM approach and exemplary incoherent motion (IM) model parameter estimation techniques described herein.

FIG. 13 compares the results of the IVIM and IM-FBM approaches with bar plots that show the CNR between the two lesion's internal components on the f maps. By using our IM-FBM approach, we achieved an average improvement in the CNR between the two internal components of 19.3% over the IVIM approach. In particular, FIG. 13 illustrates bar plots of the CNR between the two lesion's internal components on the f maps as achieved by the IVIM approach (plots 1310a, 1310b and 1310c) and by the IM-FBM approach (plots 1320a, 1320b and 1320c). With the IM-FBM approach, an average improvement in the CNR between the two internal components of 19.3% over the IVIM approach was achieved.

All definitions, as defined and used herein, should be understood to control over dictionary definitions, and/or ordinary meanings of the defined terms.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

Use of ordinal terms such as "first," "second," "third," etc., in the claims to modify a claim element does not by itself connote any priority, precedence, or order of one claim element over another or the temporal order in which acts of a method are performed. Such terms are used merely as labels to distinguish one claim element having a certain name from another element having a same name (but for use of the ordinal term).

The phraseology and terminology used herein is for the purpose of description and should not be regarded as limiting. The use of "including," "comprising," "having," "containing", "involving", and variations thereof, is meant to encompass the items listed thereafter and additional items.

Having described several embodiments of the techniques described herein in detail, various modifications, and improvements will readily occur to those skilled in the art. Such modifications and improvements are intended to be within the spirit and scope of the disclosure. Accordingly, the foregoing description is by way of example only, and is not intended as limiting. The techniques are limited only as defined by the following claims and the equivalents thereto.

What is claimed is:

1. A method of determining a set of parameter estimates for an incoherent motion model from diffusion-weighted magnetic resonance data of a portion of a biological body, the method comprising:
  (A) determining, based at least in part on the diffusion-weighted magnetic resonance data, a first set of parameter estimates for a plurality of voxels associated with one or more images to be generated, the first set of parameter estimates comprising, for each of the plurality of voxels, estimates for a slow diffusion parameter, a fast diffusion parameter, and a fractional diffusion parameter indicating a fraction of slow diffusion to fast diffusion in a respective voxel;
  (B) determining a second set of parameter estimates by stochastically perturbing the first set of parameter estimates;
  (C) determining a third set of parameter estimates based, at least in part, on fusing the first set of parameter estimates and the second set of parameter estimates using a binary cut graph technique;
  (D) determining whether at least one criterion associated with the third set of parameter estimates is satisfied;
  (E) performing acts (B)-(C) using the third set of parameter estimates as the first set of parameter estimates if the at least one criterion is not satisfied; and
  (F) generating the one or more images based, at least in part, on the third set of parameter estimates if the at least one criterion has been satisfied.

2. The method of claim 1, wherein the diffusion-weighted magnetic resonance data is obtained at a plurality of non-zero b-values.

3. The method of claim 1, wherein determining the first set of parameter estimates comprises using a spatial homogeneity prior based, at least in part, on information from adjacent voxels in the plurality of voxels.

4. The method of claim 3, wherein determining the first set of parameter estimates using the spatial homogeneity prior comprises defining the spatial homogeneity prior, at least in part, using a robust L1-norm.

5. The method of claim 1, wherein determining the second set of parameter estimates comprises using a bootstrap resampling technique that includes the stochastic perturbation of the first set of parameter estimates.

6. The method of claim 1, wherein determining the third set of parameter estimates comprises fusing the first set of parameter estimates and the second set of parameter estimates by selecting parameter estimates from either the first set of parameter estimates or the second set of parameter estimates such that the third set of parameter estimates better fits the diffusion-weighted magnetic resonance data.

7. The method of claim 1, wherein using a binary cut graph technique comprises representing each parameter estimate in the first set of parameter estimates and the second set of parameter estimates as a node and assigning edge weights based, at least in part, on a likelihood of the respective parameter estimate given the diffusion-weighted magnetic resonance data and/or differences between at least one parameter estimate of a given voxel and at least one corresponding parameter estimate of one or more adjacent voxels.

8. The method of claim 1, wherein outputting an indication of the third set of parameter estimates comprises outputting one or more images based, at least in part, on the third set of parameter estimates.

9. The method of claim 1, wherein determining whether the at least one criterion is satisfied comprises determining whether a rate of change of at least one parameter estimate from the third set of parameter estimates relative to a previous estimate of the at least one parameter estimate is less than a threshold value.

10. The method of claim 1, wherein determining whether the at least one criterion is satisfied comprises determining whether a value of an objective function used to fuse the first set of parameter estimates and the second set of parameter estimates is less than a threshold value.

11. The method of claim 1, wherein using the binary cut graph technique involves an energy optimization and wherein determining whether the at least one criterion is satisfied comprises determining whether a reduction in energy between two successive iterations of performing acts (B)-(C) is below a threshold value.

12. At least one non-transitory computer readable storage medium encoded with a plurality of instructions that, when executed by at least one computer processor, perform a method of determining a set of parameter estimates for an incoherent motion model from diffusion-weighted magnetic resonance data of a portion of a biological body, the method comprising:
  (A) determining, based at least in part on the diffusion-weighted magnetic resonance data, a first set of parameter estimates for a plurality of voxels associated with one or more images to be generated, the first set of parameter estimates comprising, for each of the plurality of voxels, estimates for a slow diffusion parameter, a fast diffusion parameter, and a fractional diffusion parameter indicating a fraction of slow diffusion to fast diffusion in a respective voxel;
  (B) determining a second set of parameter estimates by stochastically perturbing the first set of parameter estimates;
  (C) determining a third set of parameter estimates based, at least in part, on fusing the first set of parameter estimates and the second set of parameter estimates using a binary cut graph technique;
  (D) determining whether at least one criterion associated with the third set of parameter estimates is satisfied;
  (E) performing acts (B)-(C) using the third set of parameter estimates as the first set of parameter estimates if the at least one criterion is not satisfied; and
  (F) generating the one or more images based, at least in part, on the third set of parameter estimates if the at least one criterion has been satisfied.

13. At least one computer, comprising:
  at least one computer processor; and
  at least one storage device configured to store a plurality of instructions that, when executed by the at least one computer processor, perform a method of determining a set of parameter estimates for an incoherent motion model from diffusion-weighted magnetic resonance data of a portion of a biological body, the method comprising:
    (A) determining, based at least in part on the diffusion-weighted magnetic resonance data, a first set of parameter estimates for a plurality of voxels associated with one or more images to be generated, the first set of parameter estimates comprising, for each of the plurality of voxels, estimates for a slow diffusion parameter, a fast diffusion parameter, and a fractional diffusion parameter indicating a fraction of slow diffusion to fast diffusion in a respective voxel;

(B) determining a second set of parameter estimates by stochastically perturbing the first set of parameter estimates;

(C) determining a third set of parameter estimates based, at least in part, on fusing the first set of parameter estimates and the second set of parameter estimates using a binary cut graph technique;

(D) determining whether at least one criterion associated with the third set of parameter estimates is satisfied;

(E) performing acts (B)-(C) using the third set of parameter estimates as the first set of parameter estimates if the at least one criterion is not satisfied; and (F) generating the one or more images based, at least in part, on the third set of parameter estimates if the at least one criterion has been satisfied.

14. The at least one computer of claim 13, wherein the diffusion-weighted magnetic resonance data is obtained at a plurality of non-zero b-values.

15. The at least one computer of claim 13, wherein determining the first set of parameter estimates comprises using a spatial homogeneity prior based, at least in part, on information from adjacent voxels in the plurality of voxels.

16. The at least one computer of claim 13, wherein determining the second set of parameter estimates comprises using a bootstrap resampling technique that includes the stochastic perturbation of the first set of parameter estimates.

17. The at least one computer of claim 13, wherein determining the third set of parameter estimates comprises fusing the first set of parameter estimates and the second set of parameter estimates by selecting parameter estimates from either the first set of parameter estimates or the second set of parameter estimates such that the third set of parameter estimates better fits the diffusion-weighted magnetic resonance data.

* * * * *

UNITED STATES PATENT AND TRADEMARK OFFICE
CERTIFICATE OF CORRECTION

PATENT NO. : 9,492,101 B2
APPLICATION NO. : 14/431649
DATED : November 15, 2016
INVENTOR(S) : Simon K. Warfield et al.

It is certified that error appears in the above-identified patent and that said Letters Patent is hereby corrected as shown below:

In the Specification

At Column 1, Line 11, please insert the following paragraph:
--STATEMENT OF RIGHTS TO INVENTIONS MADE UNDER FEDERALLY SPONSORED RESEARCH
This invention was made with government support under grant numbers EB008015, EB013248, LM010033, and HD018655, awarded by the National Institutes of Health. The government has certain rights in the invention.--

Signed and Sealed this
Second Day of April, 2024

Katherine Kelly Vidal
*Director of the United States Patent and Trademark Office*